United States Patent
Ju et al.

(10) Patent No.: US 10,428,355 B2
(45) Date of Patent: Oct. 1, 2019

(54) PRODUCTION OF ARABITOL

(71) Applicants: Lu-Kwang Ju, Akron, OH (US); Abdullah Al Loman, Akron, OH (US)

(72) Inventors: Lu-Kwang Ju, Akron, OH (US); Abdullah Al Loman, Akron, OH (US)

(73) Assignee: THE UNIVERSITY OF AKRON, Akron, OH (US)

( * ) Notice: Subject to any disclaimer, the term of this patent is extended or adjusted under 35 U.S.C. 154(b) by 0 days.

(21) Appl. No.: 15/648,806

(22) Filed: Jul. 13, 2017

(65) Prior Publication Data

US 2018/0016603 A1    Jan. 18, 2018

Related U.S. Application Data

(60) Provisional application No. 62/362,322, filed on Jul. 14, 2016.

(51) Int. Cl.
   *C12P 7/18*  (2006.01)

(52) U.S. Cl.
   CPC ..................... *C12P 7/18* (2013.01)

(58) Field of Classification Search
   CPC .......................................... C12P 7/18
   See application file for complete search history.

(56) References Cited

U.S. PATENT DOCUMENTS

| 9,062,329 B2 | 6/2015 | Ju |
| 2015/0118730 A1 | 4/2015 | Ju et al. |
| 2016/0304925 A1 | 10/2016 | Ju |

OTHER PUBLICATIONS

Kumdam et al., AMB Express 3:23, pp. 1-12, 2013.*

* cited by examiner

*Primary Examiner* — Delia M Ramirez
(74) *Attorney, Agent, or Firm* — Renner Kenner Greive Bobak Taylor & Weber

(57) ABSTRACT

A method for producing arabitol may include providing a fermentation culture having a microorganism and a carbon source; allowing the microorganism to ferment the carbon source; monitoring a process condition of said step of allowing the microorganism to ferment the carbon source; and collecting a product from the fermentation culture after said step of monitoring a process condition indicates that a predetermined change in the process condition has occurred. Other methods may include steps of providing soybean-based lignocellulosic hydrolysate as a carbon source for a fermentation culture, and modifying the pH of one or more of the growth phase and the stationary phase of a fermentation process.

12 Claims, 10 Drawing Sheets

PRODUCTION OF ARABITOL

CROSS-REFERENCE TO RELATED APPLICATIONS

The present application claims the benefit of U.S. Provisional Patent Application No. 62/362,322, filed Jul. 14, 2016, which is incorporated herein by reference.

FIELD OF THE INVENTION

The present invention relates to improved production of arabitol. The present invention further relates to production of arabitol from a mixture of hexoses and pentoses. The present invention further relates to process conditions for the production of arabitol.

BACKGROUND OF THE INVENTION

Arabitol is a five carbon sugar alcohol with one hydroxyl group on each carbon. It is a stereoisomer of xylitol, a well-known low calorie sugar substitute. Xylitol has anti-cariogenic characteristics and therefore has been used in commercial products such as chewing gum, toothpaste, lozenges, and low calorie sweeteners. Arabitol also inhibits the growth and acid production by cariogenic bacteria and therefore is a potential alternative to xylitol for these products.

Arabitol has been produced in the laboratory by fermentation of osmophilic yeast since at least the 1950's when first detected polyol in the fermentation residue of cane blackstrap molasses by baker's yeast. In the last 60 years, arabitol has also been produced from glucose or sucrose by various osmophilic yeast, but these processes lack the productivity necessary for widespread industrial production of arabitol U.S. Pat. No. 9,062,329 discloses a process of producing arabitol utilizing a medium containing microorganisms, such as yeast, and a carbon source, such as a hydrolysate of plant biomass.

U.S. Pub. No. 2016/0304925 discloses the hydrolysis of soybean flour carbohydrate using an enzyme with activities of cellulase, xylanase, polygalacturonase, pectinase, α-galactosidase, and sucrose. The process generates a valuable soy protein product and a liquid hydrolysate. The hydrolysate contains mixtures of glucose, galactose, fructose, xylose, arabinose, and other minor carbohydrates.

SUMMARY OF THE INVENTION

In a first embodiment, the present invention provides a method for producing arabitol including providing a fermentation culture having a microorganism and a carbon source; allowing the microorganism to ferment the carbon source; monitoring a process condition of said step of allowing the microorganism to ferment the carbon source; and collecting a product from the fermentation culture after said step of monitoring a process condition indicates that a predetermined change in the process condition has occurred.

In a second embodiment, the present invention provides a method for producing arabitol including allowing an enzyme to hydrolyze a lignocellulosic biomass selected from one or more of soybean flour, soybean hull, soybean molasses, and soybean okara, to obtain a lignocellulosic hydrolysate; providing the lignocellulosic hydrolysate as a carbon source for a fermentation culture having a microorganism therein; allowing the microorganism to ferment the lignocellulosic hydrolysate; and collecting a product having 80 parts by weight or greater arabitol based on 100 total parts by weight of all polyols produced, following said step of allowing the microorganism to ferment the lignocellulosic hydrolysate wherein In a third embodiment, a method for producing arabitol including combining a feedstock having a carbon source with a microorganism to form a fermentation culture to ferment the carbon source with the microorganism by a fermentation process, the fermentation process having a growth phase and a stationary phase; modifying the pH of one or more of the growth phase and the stationary phase; and obtaining a product including arabitol, where said step of obtaining achieves a greater arabitol yield than a process without said step of modifying the pH.

In a fourth embodiment, the present invention provides a method combining any one or more steps as in any of the above embodiments, In a fifth embodiment, the present invention provides a method as in any of the above embodiments, wherein the process condition is the dissolved oxygen concentration of the fermentation process, wherein said predetermined change includes the dissolved oxygen concentration increasing a relative amount of 100% or more.

In a sixth embodiment, the present invention provides a method as in any of the above embodiments, wherein said step of monitoring a process condition includes controlling the dissolved oxygen concentration to a controlled dissolved oxygen concentration.

In a seventh embodiment, the present invention provides a method as in any of the above embodiments, wherein said predetermined change includes the dissolved oxygen concentration increasing to an absolute amount of 15% or more.

In an eighth embodiment, the present invention provides a method as in any of the above embodiments, further comprising modifying the fermentation culture after said step of monitoring a process condition indicates that a predetermined change in the process condition has occurred.

In a ninth embodiment, the present invention provides a method as in any of the above embodiments, wherein said step of modifying the fermentation culture includes adding additional carbon source to the fermentation culture.

In a tenth embodiment, the present invention provides a method as in any of the above embodiments, wherein the microorganism and the carbon source are provided by a first batch of a feedstock containing the microorganism and the carbon source, wherein said step of modifying the fermentation culture includes adding to the fermentation culture a second batch of the feedstock containing additional amounts of the microorganism and the carbon source.

In an eleventh embodiment, the present invention provides a method as in any of the above embodiments, wherein the product includes 80 parts by weight or greater arabitol based on 100 total parts by weight of all polyols produced.

In a twelfth embodiment, the present invention provides a method as in any of the above embodiments, wherein the process condition is the arabitol concentration of the fermentation culture, wherein the predetermined change in the process condition is the arabitol concentration of the fermentation culture increasing to a predetermined amount.

In a thirteenth embodiment, the present invention provides a method as in any of the above embodiments, the microorganism being osmophilic yeast of one or more of the genera *Debaryomyces* and *Metschnikowia*.

In a fourteenth embodiment, the present invention provides a method as in any of the above embodiments, further comprising a step of adding a potassium-containing mineral following said step of allowing the microorganism to ferment the lignocellulosic hydrolysate and prior to said step of collecting a product, wherein the arabitol concentration of the collected product is higher compared to a process wherein a potassium-containing mineral is not added.

In a fifteenth embodiment, the present invention provides a method as in any of the above embodiments, further comprising a step of adding a potassium-containing mineral following said step of allowing the microorganism to ferment the lignocellulosic hydrolysate and prior to said step of collecting a product, wherein the arabitol concentration of the collected product is higher compared to a process wherein a calcium-containing mineral or a magnesium-containing mineral is added.

In a sixteenth embodiment, the present invention provides a method as in any of the above embodiments, wherein the dissolved oxygen concentration during said step of allowing the microorganism to ferment the lignocellulosic hydrolysate is sufficiently high as to achieve substantially complete fermentation of all hexoses and pentoses in the lignocellulosic hydrolysate, the collected product having 90 parts by weight or greater arabitol based on 100 total parts by weight of all polyols produced.

In a seventeenth embodiment, the present invention provides a method as in any of the above embodiments, wherein the lignocellulosic hydrolysate includes one or more of 1 wt. % or more amino acids, 1 wt. % or more peptides, and 1 wt. % or more proteins, thereby minimizing the need for cellular amino acid synthesis in the microorganism, thereby increasing arabitol production by maintaining the available intermediates from the pentose phosphate pathway for the production of arabitol.

In an eighteenth embodiment, the present invention provides a method as in any of the above embodiments, wherein said step of modifying the pH includes maintaining the growth phase at a pH in a range of from 5.5 or more to 8 or less.

In a nineteenth embodiment, the present invention provides a method as in any of the above embodiments, wherein said step of modifying the pH includes maintaining the stationary phase at a pH in a range of from 3.5 or more to 4.5 or less.

In a twentieth embodiment, the present invention provides a method as in any of the above embodiments, wherein said step of modifying the pH includes maintaining the growth phase at a pH in a range of from 5.5 or more to 8 or less and maintaining the stationary phase at a pH in a range of from 3.5 or more to 4.5 or less.

In a twenty-first embodiment, the present invention provides a method as in any of the above embodiments, further comprising the step of adding additional carbon source to the fermentation culture thereby preventing the consumption of arabitol as a carbon source, wherein the method achieves increasing arabitol production in both the growth phase and the stationary phase.

BRIEF DESCRIPTION OF THE DRAWINGS

Advantages of the present invention will become better understood with regard to the following description, appended claims, and accompanying drawings wherein:

DETAILED DESCRIPTION OF ILLUSTRATIVE EMBODIMENTS

Figure 1:
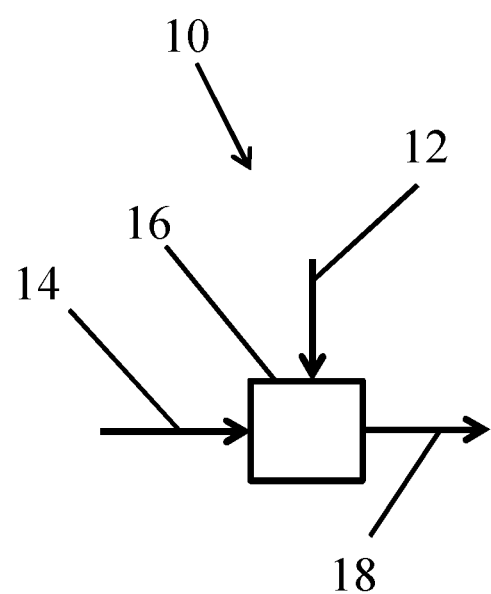
FIG. 1 is a schematic according to one or more embodiments of the invention.

With reference to FIG. 1, one or more embodiments of the invention provide a fermentation process, generally indicated by the numeral 10, where a feedstock 12 is combined with a microorganism stream 14 in a fermentation vessel 16 to produce a product stream 18. Feedstock 12 includes the components necessary for microorganisms within microorganism stream 14 to produce product stream 18 by a fermentation process.

One or more embodiments of the invention may be described as industrial fermentation, which is generally known as the intentional use of fermentation by microorganisms to make products useful to humans. As generally known to those skilled in the art, a complete fermentation cycle includes sequential steps of lag phase, growth phase, stationary phase, and death phase. Lag phase generally relates to the initial mixing of feedstock 12 and microorganism stream 14 before the microorganisms in microorganism stream have become acclimated to the new environment and had all necessary enzymes to support active growth. Following the lag phase, the rate of growth of the microorganisms in microorganism stream 14 has increased to the maximum rate based on the given nutrients and operating conditions for a period of time, known as the growth phase or exponential growth phase. At the end of the growth phase, the rate of growth of the microorganisms slows, due to continuously falling concentrations of nutrients and/or a continuous accumulation of toxic substances. The growth decelerates until the fermentation culture enters a stationary phase. In the stationary phase, the biomass may remain constant or substantially constant. The fermentation culture will remain in the stationary phase until sufficient consumption of nutrients or increased concentration of toxins causes the microorganisms to begin to die off, entering the death phase.

Figure 2:
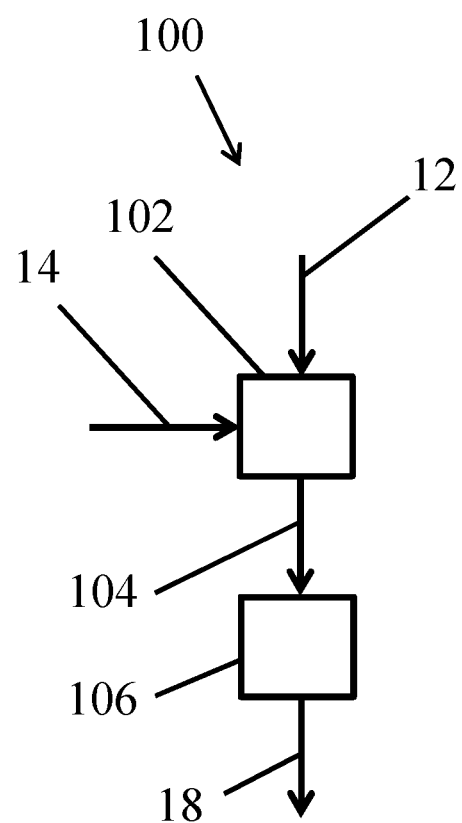
FIG. 2 is a schematic according to one or more embodiments of the invention.

As will be described further herein below, one or more embodiments of the present invention involve manipulating one or more of the lag phase, growth phase, stationary phase, and death phase. Embodiments may include manipulating one or more of the phases to achieve a commercially viable process. In one or more embodiments, the selection of a particular feedstock accomplishes prolonged active cell growth in a growth phase. In one or more embodiments, this prolonged active cell growth results in the production of arabitol at a higher productivity. In one or more embodiments, a fermentation culture may be maintained in the growth phase for a predetermined amount of time by one or more of removing microorganisms, adding nutrients, and removing toxins. In one or more embodiments, a fermentation culture may be similarly maintained in the stationary phase for a predetermined amount of time. In one or more embodiments, the death phase may be avoided or substantially avoided prior to collection of a product stream. Advantageously, one or more embodiments are able to achieve increasing arabitol production in both the growth phase and the stationary phase. As discussed herein below, this may include one or more of providing sufficient amounts of the carbon source to the growth phase, providing sufficient amounts of the carbon source to the stationary phase, manipulating the pH of the growth phase, and manipulating the pH of the stationary phase. The steps of providing sufficient amounts of the carbon source to the growth phase and providing sufficient amounts of the carbon source to the stationary phase may be to not allow the arabitol to be consumed as the carbon source With reference to FIG. 2, one or more embodiments of the invention provide a fermentation process, generally indicated by the numeral 100, where feedstock 12 is combined with microorganism stream 14 in a first vessel 102. In first vessel 102, one or more of the lag phase, growth phase, and stationary phase occurs or substantially occurs for the microorganisms in microorganism stream 14. A product stream 104 from first vessel 102 is provided to a second vessel 106, where one or more of the growth phase, stationary phase, and death phase may occur. This results in a product stream 18. In one or more embodiments, one or more of the stationary phase and death phase may occur or substantially occur in a third vessel (not shown). In one or more embodiments, the death phase may occur or substantially occur in a fourth vessel (not shown). As used here, "substantially occur" is meant that at least the majority of the one or more phases would occur in a particular vessel, but the remainder of the phase may occur in a different vessel.

Feedstock 12, which may also be referred to as carbon source 12, carbon-containing stream 12, or media 12, must contain a carbon source, a nitrogen source, and water. The carbon source and the nitrogen source may optionally be provided within one or more of a mixture of carbon sources, a mixture of nitrogen sources, and a mixture of carbon sources and nitrogen sources. Feedstock 12 may also contain one or more salts and one or more micronutrients.

In one or more embodiments, feedstock 12 may contain one or more hydrolysates of lignocellulosic biomass, where the one or more hydrolysates may be referred to as lignocellulosic hydrolysates. In one or more embodiments, a lignocellulosic biomass is soybean flour and a corresponding hydrolysate is soybean flour hydrolysate (SFH). In one or more embodiments, a lignocellulosic biomass is soybean hulls and a corresponding hydrolysate is soybean hull hydrolysate (SHH). In one or more embodiments, a lignocellulosic biomass includes soybean flour and soybean hulls and a corresponding hydrolysate is mixed soybean hydrolysate. In one or more embodiments, a lignocellulosic biomass may be characterized as a soybean-based lignocellulosic biomass and a corresponding hydrolysate may be characterized as a soybean-based hydrolysate.

The hydrolysate may be prepared by a hydrolysis process, also known as hydrolyzing, utilizing an enzyme containing activities of cellulase, xylanase, polygalacturonase, pectinase, α-galactosidase, and sucrase (or invertase). The hydrolysate may be prepared using the enzyme produced by *Aspergillus niger*. One or more aspects of a hydrolysate, such as time, temperature, and pH of a method of producing the hydrolysate, may be further disclosed in U.S. Publication No. 2016/0304925 and U.S. Publication No. 2015/0118730, which are each incorporated herein by reference. A process of producing a hydrolysate may generate two product streams: a valuable soy protein product of high protein content and minimized indigestible carbohydrate, and a liquid hydrolysate. The hydrolysate, for use as fermentation feedstock, may contain mixtures of one or more of glucose, galactose, fructose, xylose, arabinose, and other minor carbohydrates as a carbon source. The hydrolysate may also contain soluble proteinaceous substances as a nitrogen source.

Other exemplary lignocellulosic biomasses include soybean meal and soybean waste products and byproducts, such as molasses generated from the processes for soy protein concentrate (SPC) production, and soybean okara created during production of soy protein isolate (SPI) and soybean milk. Other exemplary lignocellulosic biomasses include canola meal, cottonseed meal, flax seed meal, sunflower seed meal, pumpkin seed meal, hemp seed meal, chia seed meal, neem seed meal, citrus seed meal, watermelon seed meal, and other seed meals, and the hulls/husks of these seeds, and other biomass offering carbohydrate and protein to support cell growth and arabitol production.

In one or more embodiments, a lignocellulosic hydrolysate may be characterized as containing mixtures of multiple hexoses and pentoses. In one or more embodiments, a lignocellulosic hydrolysate may be characterized as a complex mixture of sugars and organic nitrogenous compounds. In one or more embodiments, a lignocellulosic hydrolysate may be characterized as a renewable biorefinery feedstock.

In one or more embodiments, a lignocellulosic hydrolysate may be characterized as having a high content of amino acids. In one or more embodiments, a lignocellulosic hydrolysate may be characterized as having a high content of peptides. In one or more embodiments, a lignocellulosic hydrolysate may be characterized as having a high content of proteins. As used here, the term "high" may be defined as having 1 wt. % or more of the particular component.

In one or more embodiments, a lignocellulosic hydrolysate may be characterized as being rich in cellulose and hemicellulose contents. In one or more embodiments, a lignocellulosic hydrolysate, such as soybean meal, flour, and hull, may be characterized as containing pectic polysaccharides and galacto-oligosaccharides. A biomass hydrolysate may be designed to have a particular carbohydrate composition, including hexose-to-pentose ratios, which may be calculated based on any of the percentage amounts disclosed herein below for feedstock 12.

In one or more embodiments, a lignocellulosic hydrolysate may be characterized by its protein content, which can be an important factor to fermentation design. In one or more embodiments, a lignocellulosic hydrolysate may have a protein content of 1 wt. % or more, in other embodiments, 2 wt. % or more, and in other embodiments, 5 wt. % or more.

In one or more embodiments, the nitrogen source of feedstock 12 may by organic nitrogen. Organic nitrogen may be beneficial for cell growth and metabolism. In addition, the amount of nitrogen in feedstock 12 affects the ratio of carbon to nitrogen sources and the limiting substrate for cell growth. This is on the basis that carbon-limiting media are not ideal for production of secondary metabolites while nitrogen-limiting media may be less efficient for primary metabolite production.

Where feedstock 12 includes SFH, the presence of rich organic C and N sources in the SFH-based media can support and prolong the active cell growth. In these embodiments, the aromatic amino acid synthesis for cell growth diverts away the shared precursors for arabitol production. Without being bound by any theory, the high contents of amino acids, peptides, and/or proteins provided by certain feedstocks 12, such as SFH minimize the need of cellular amino acid synthesis, thus leaving more intermediates in the pentose phosphate pathway for arabitol production. Feedstocks 12 with rich organic carbon and nitrogen sources, such as SFH, promote arabitol production with high yield and productivity.

As further explanation, arabitol synthesis involves the pentose phosphate pathway. Primary physiological roles of this pathway are for synthesis of ribose, for the subsequent synthesis of nucleotides and nucleic acids (RNA and DNA), and for synthesis of precursors to aromatic amino acids, for subsequent protein/enzyme synthesis. These main products of pentose phosphate pathway are essential for cell growth; therefore, the pathway is under growth-related metabolic regulation and is operating at higher reaction rates in actively growing cells. Embodiments where a fermentation process maintains the microorganism, such as yeast, cells at a longer period of active growth may thus produce arabitol at a higher productivity.

In one or more embodiments, feedstock 12 may be characterized by its sugar composition. Different sugars affect cell growth and product conversion by microorganisms. As said above, feedstock 12 may include hexose and pentose sugars commonly found in a lignocellulosic hydrolysate. Glucose, fructose and galactose are exemplary common hexoses, and xylose and arabinose are exemplary common pentoses.

In one or more embodiments, feedstock 12 includes 30 wt. % or less, in other embodiments, 25 wt. % or less, in other embodiments, 20 wt. % or less, in other embodiments, 15 wt. % or less, in other embodiments, 12 wt. % or less, in other embodiments, 10 wt. % or less, in other embodiments, 5 wt. % or less, in other embodiments, 3 wt. % or less, pentoses with respect to weight of the total sugars. In one or more of these embodiments, the balance percentage may be hexoses.

In one or more embodiments, feedstock 12 includes 5 wt. % or more, in other embodiments, 20% or more, in other embodiments, 40% or more, in other embodiments, 70 wt. % or more, in other embodiments, 75 wt. % or more, in other embodiments, 80 wt. % or more, in other embodiments, 85 wt. % or more, in other embodiments, 88 wt. % or more, in other embodiments, 90 wt. % or more, in other embodiments, 95 wt. % or more, in other embodiments, 100 wt. % or more, hexoses with respect to weight of the total sugars. In one or more of these embodiments, the balance percentage may be pentoses.

One or more embodiments of the invention provide higher sugar consumption rate and arabitol yield using increasing hexose-to-pentose ratios.

In one or more embodiments, feedstock 12 includes from 20 wt. % or more to 75 wt. % or less, in other embodiments, 40 wt. % or more to 75 wt. % or less, in other embodiments, 50 wt. % or more to 75 wt. % or less, in other embodiments, 65 wt. % or more to 75 wt. % or less, glucose with respect to weight of the total sugars. In one or more embodiments, feedstock 12 includes 15 wt. % or more, in other embodiments, 25 wt. % or more, in other embodiments, 40 wt. % or more, in other embodiments, 55 wt. % or more, in other embodiments, 65 wt. % or more, in other embodiments, 75 wt. % or more, glucose with respect to weight of the total sugars. In one or more embodiments, feedstock 12 includes 75 wt. % or less, in other embodiments, 65 wt. % or less, in other embodiments, 55 wt. % or less, in other embodiments, 40 wt. % or less, in other embodiments, 25 wt. % or less, in other embodiments, 15 wt. % or less, glucose with respect to weight of the total sugars.

Because microorganisms generally utilize catabolite repression, thereby observing a particular sequence of sugar consumption, the sugar composition of a feedstock 12 may affect cell growth and arabitol production. In one or more embodiments, a microorganism undergoes catabolite repression with the following order of consumption: glucose first, then fructose, then galactose, then xylose, and then arabinose.

In one or more embodiments, a fermentation method is performed for a length of time that will allow the microorganisms to consume hexoses, in the order of glucose, then fructose, and finally galactose, but that will not allow the microorganisms to consume the pentoses, e.g. xylose and arabinose.

One or more embodiments of the invention provide higher sugar consumption rate and arabitol yield with increasing amounts of glucose weight percentage in feedstock 12. In one or more embodiments, feedstock 12 includes glucose as at least 50 wt. % of the hexoses in feedstock 12, and an arabitol yield of at least 45% is achieved. In one or more embodiments, feedstock 12 includes glucose as at least 50 wt. % of the hexoses in feedstock 12, and an arabitol yield of at least 46.2% is achieved. As used herein, the term "arabitol yield may be defined as the percent conversion of total sugars in a feedstock to arabitol.

In one or more embodiments, feedstock 12 may contain one or more lignocellulosic hydrolysates supplemented with an additional sugar source. This may have the effect of increasing the carbon-to-nitrogen concentration ratio (C/N) ratio of feedstock 12 to thereby increase the arabitol yield. This increase is believed to be due to higher arabitol yield at the stationary phase when no sugars are consumed for cell growth. Exemplary additional sugars are disclosed below.

In one or more embodiments, feedstock 12 includes 1 wt. % or more, in other embodiments, 5 wt. % or more, in other embodiments, 10 wt. % or more, in other embodiments, 20 wt. % or more, in other embodiments, 40 wt. % or more, in other embodiments, total sugars with respect to weight of the entire feedstock 12. Feedstocks 12 above 5 wt. % total sugars with respect to weight of the entire feedstock 12 may be considered concentrated feedstocks. In one or more embodiments, a concentrated feedstock may achieve higher productivity of arabitol in a fermentation process than a feedstock that is not concentrated.

In one or more embodiments, feedstock 12 includes a mineral supplementation. In one or more embodiments, feedstock 12 with a mineral supplementation improves cell growth and arabitol production compared to a feedstock 12 without a mineral supplementation. In one or more embodiments, feedstock 12 with a first mineral supplementation improves cell growth and arabitol production compared to a feedstock 12 with a second mineral supplementation different from the first mineral supplementation.

Embodiments of the invention advantageously employ supplementing feedstock 12 with potassium to significantly improve cell growth and arabitol production. However, supplementing with calcium, e.g. calcium chloride, and magnesium, e.g. magnesium sulfate, was not found to significantly improve cell growth and arabitol production. The advantageous benefit of potassium may be said to be unexpected in view of prior teachings as there was not previously a predictable theoretical basis for expecting one certain mineral to have a more positive effect than others.

Exemplary advantageous mineral supplementations including potassium include potassium phosphate, potassium biphosphate, potassium chloride, potassium sulfate, potassium nitrate, potassium carbonate, potassium acetate, and potassium hydroxide.

Other potential mineral supplementations may include calcium chloride, magnesium chloride, magnesium nitrate, magnesium acetate, magnesium sulfate, manganese sulfate, manganese chloride, manganese nitrate, manganese acetate, iron chloride, iron nitrate, sodium chloride, sodium sulfate, sodium phosphate, zinc chloride, and zinc sulfate.

In one or more embodiments, a mineral supplementation may be added to feedstock 12 at an amount of from 1 g/L or more to 5 g/L or less, in other embodiments, from 2 g/L or more to 4 g/L or less, and in other embodiments, from 2.2 g/L or more to 2.8 g/L or less.

In one or more embodiments, a mineral supplementation to feedstock 12 improves maximum cell concentration by an amount of 20% or more, in other embodiments, 15% or more, and in other embodiments, 10% or more, compared to a system without a mineral supplementation. In one or more embodiments, a mineral supplementation to feedstock 12 improves maximum cell concentration from 9.2±0.3 g/L to. 10.2±0.4 g/L. In one or more embodiments, a mineral supplementation to feedstock 12 improves arabitol yield by an amount of 40% or more, in other embodiments, 35% or more, in other embodiments, 30% or more, and in other embodiments, 25% or more, compared to a system without a mineral supplementation. In one or more embodiments, a mineral supplementation to feedstock 12 improves arabitol yield from 11±0.6 g/L to 14.1±0.4 g/L.

Microorganisms in microorganism stream 14 produce product stream 18 from feedstock 12 by a fermentation process. As generally described above, and as known to those skilled in the art, fermentation methods are metabolic processes that generally include the conversion of sugar to acids and gases, or alcohol. The particularly desired product for embodiments of the present invention is arabitol.

In one or more embodiments, the microorganisms in microorganism stream 14 are yeast. In one or more embodiments, the microorganisms in microorganism stream 14 are osmophilic yeast. In one or more embodiments, the microorganisms in microorganism stream 14 may be one or more of any microorganism (e.g. non-osmophilic yeast, bacteria, fungi) capable of producing arabitol.

In one or more embodiments, the microorganisms in microorganism stream 14 are yeasts selected from the genera *Debaryomyces*, *Metschnikowia*, and *Geotrichum*, and combinations thereof. In one or more embodiments, it may be preferable to use yeast of the genera *Debaryomyces* and *Metschnikowia*, as such strains have been discovered to produce predominantly arabitol, based on total polyol content. Certain *Geotrichum* strains, while producing a major amount of arabitol, have also been found to produce minor amounts of other polyols such as mannitol.

An exemplary species or strain of the genera *Debaryomyces* is *Debaryomyces hansenii*. An exemplary strain of *Debaryomyces hansenii* is *Debaryomyces hansenii* SBP-1 (NRRL Y-7483). Other *Debaryomyces hansenii* strains include SBP-2 (NRRL Y-1015), SBP-3 (NRRL Y-10452), SBP-5 (NRRL Y-1448), SBP-8 (NRRL Y-1454), SBP-15 (NRRL Y-10150).

An exemplary species or strain of the genera *Metschnikowia* is *Metschnikowia zobellii*. An exemplary strain of *Metschnikowia zobellii* is NRRL Y-5387.

Exemplary species or strains of the genera *Geotrichum* are *Geotrichum candidum*, *Geotrichum fermentans*, and *Geotrichum cucujoidarum*. Some exemplary strains of *Geotrichum candidum* are NRRL Y-714, NRRL Y-1282, NRRL Y-17010, and NRRL Y-2071. An exemplary strain of *Geotrichum cucujoidarum* is NRRL Y-27731. An exemplary strain of *Geotrichum fermentans* is NRRL Y-17567.

In one or more embodiments, the concentration of the microorganisms utilized in a lag phase may range from 0.01 g/L or more to 5 g/L or less, in other embodiments, from 0.1 g/L or more to 3 g/L or less, and in other embodiments, from 0.5 g/L or more to 2 g/L or less, of the fermentation medium. The maximum concentration of the microorganisms reached during a growth phase may range from 5 g/L or more to 60 g/L or less, in other embodiments, from 10 g/L or more to 50 g/L or less, and in other embodiments, from 20 g/L or more to 40 g/L or less, of the fermentation medium.

In one or more embodiments, a particular microorganism may be selected based on a desired catabolite repression. In one or more embodiments, a microorganism is selected in order to achieve the following order of consumption: glucose, fructose, galactose, xylose, and arabinose.

As discussed above, the fermentation may take place in a single fermentation vessel, e.g. vessel 16, or a series of one or more fermentation vessels, e.g. first vessel 102 and second vessel 106. In one or more embodiments, the one or more fermentation vessels may be characterized by a desired volume.

In one or more embodiments, one or more fermentation vessels may be characterized by a working volume, defined as the amount of fermentation medium present as a percentage of the total available volume in the fermentation vessel. In one or more embodiments, one or more fermentation vessels may be characterized by a working volume in a range of from 5% or more to 70% or less, in other embodiments, from 10% or more to 50% or less, in other embodiments, from 15% or more to 30% or less, and in other embodiments, from 20% or more to 25% or less.

In one or more embodiments, one or more fermentation vessels may be characterized as being part of a soy-based biorefinery.

In one or more embodiments, a fermentation method may be operated on a continuous basis. In other embodiments, a fermentation method may be operated as a batch process. In other embodiments, a fermentation method may be operated as a fed-batch (multiple batch addition) process.

In one or more embodiments, the lag phase of a fermentation method may be characterized by a particular time. In one or more embodiments, a lag phase may occur for a substantially small time that is undetectable. In one or more embodiments, a lag phase may occur for 2 hours or more, in other embodiments, for 6 hours or more, in other embodiments, for 12 hours or more, and in other embodiments, for 18 hours or more. In one or more embodiments, a lag phase may occur for 2 hours or less, in other embodiments, for 6 hours or less, in other embodiments, for 12 hours or less, and in other embodiments, for 18 hours or less.

In one or more embodiments, the growth phase of a fermentation method may be characterized by a particular time. In one or more embodiments, a growth phase may occur for 10 hours or more, in other embodiments, for 20 hours or more, in other embodiments, for 24 hours or more, and in other embodiments, for 36 hours or more. In one or more embodiments, a growth phase may occur for 72 hours or less, in other embodiments, for 60 hours or less, in other embodiments, for 48 hours or less, and in other embodiments, for 36 hours or less. In one or more embodiments, a growth phase may occur in a range of from 10 hours or more to 72 hours or less, and in other embodiments, from 24 hours or more to 48 hours or less.

In one or more embodiments, the stationary phase of a fermentation method may be characterized by a particular time. In one or more embodiments, a stationary phase may occur for a substantially small time that is undetectable. In one or more embodiments, a stationary phase may occur for 24 hours or more, in other embodiments, for 72 hours or more, in other embodiments, for 120 hours or more, and in other embodiments, for 168 hours or more. In one or more embodiments, a stationary phase may occur for 240 hours or less, in other embodiments, for 168 hours or less, in other embodiments, for 120 hours or less, and in other embodiments, for 72 hours or less.

The time for a stationary phase may depend on C:N ratio of the substrate. In general, the higher the C:N ratio, the longer the stationary phase. As discussed elsewhere herein, a critical point may occur once the preferred carbon source is depleted, and the microorganism cells will start to consume the arabitol as the carbon source, thereby reducing the desired arabitol product produced if the process were allowed to continue without collecting the arabitol product.

In one or more embodiments, the death phase of a fermentation method may be characterized by a particular time. In one or more embodiments, a death phase may occur for a substantially small time that is undetectable. In one or more embodiments, a growth phase may occur for 6 hours or more, in other embodiments, for 12 hours or more, in other embodiments, for 24 hours or more, and in other embodiments, for 36 hours or more. In one or more embodiments, a growth phase may occur for 48 hours or less, in other embodiments, for 36 hours or less, in other embodiments, for 12 hours or less, and in other embodiments, for 6 hours or less. It is generally undesirable for a fermentation method of the present invention to allow the death phase to occur due to carbon source exhaustion. If a death phase instead occurs due to a certain pH, DO, or other non-carbon source depletion, then a longer death phase may still allow some additional arabitol production.

In one or more embodiments, a fermentation method may be characterized by the process conditions thereof. Any of the process conditions disclosed herein may be used in any fermentation vessel. One or more aspects of the process conditions may be disclosed in U.S. Pat. No. 9,062,329, which is incorporated herein by reference.

In one or more embodiments, a fermentation method may be characterized as being carbon-limiting. This generally means that the fermentation medium runs out of carbon source before running out of nitrogen source or any other nutrients essential for cell growth. In one or more embodiments, a fermentation method may be characterized as being nitrogen-limiting. This generally means that the fermentation medium can run out of nitrogen source before running out of carbon source or any other nutrients essential for cell growth.

In one or more embodiments, a fermentation method may be characterized by carbon-to-nitrogen concentration ratio (C/N). Carbon-to-nitrogen concentration ratio is based, at least in part, on the type of feedstock utilized. A carbon source, such as sugar, may be combined with the feedstock or fermentation mixture to adjust the C/N ratio. In these or other embodiments, a nitrogen source, such as peptone, may be combined with the feedstock or fermentation mixture to adjust the C/N ratio. Exemplary carbon sources, which may be described as the additional sugar disclosed above, include glycerol, glucose, fructose, galactose, xylose, arabinose, mannose, rhamnose, sucrose, and combinations thereof. Exemplary nitrogen sources include peptone, yeast extract, tryptone, malt extract, ammonium sulfate, ammonium phosphate, ammonium hydrogen phosphate, ammonium dihydrogen phosphate, ammonium nitrate, ammonium chloride, ammonium hydroxide, ammonium acetate, ammonium bicarbonate, ammonium carbonate, ammonia, urea, sodium nitrate, potassium nitrate, protein, peptides, amino acids, corn steep liquor, milk, soybean meal, soybean flour, soybean molasses, soybean milk, other seed meals, and combinations thereof.

In one or more embodiments, the C/N ratio of a fermentation mixture is 20 or more, in other embodiments, 30 or more, in other embodiments, 40 or more, in other embodiments, 50 or more, and in other embodiments, 60 or more. In one or more embodiments, the C/N ratio of a fermentation mixture is 65 or less, in other embodiments, 60 or less, in other embodiments, 50 or less, in other embodiments, 40 or less, and in other embodiments, 30 or less. In one or more embodiments, the C/N ratio of a fermentation mixture is in a range of from 20 or more to 100 or less, in other embodiments, from 30 or more to 60 or less, and in other embodiments, from 34 or more to 40 or less.

One or more embodiments of the invention provide a fermentation method with higher arabitol production when using an increased C/N ratio. One or more embodiments of the invention provide a fermentation method supporting arabitol production for twice as many days using an increased C/N ratio. One or more embodiments of the invention provide a fermentation method supporting arabitol production for 2.5 as many days using an increased C/N ratio. One or more embodiments of the invention provide a fermentation method supporting arabitol production for one additional day, in other embodiments, two additional days, and in other embodiments, three additional days, using an increased C/N ratio. One or more embodiments of the invention provide a fermentation method supporting arabitol production in both the growth phase and stationary phase for two days, in other embodiments, four days, and in other embodiments, five days, using an increased C/N ratio.

One or more embodiments of the invention provide a fermentation method with higher arabitol yield using an increased C/N ratio. As exemplified below, a first fermentation method with a C/N ratio of 23.8 may give a 34% yield, which a second fermentation method with a C/N ratio of 63 may give a 47% yield. It is believe that the increasing C/N ratio gives a higher arabitol yield when produced during the stationary phase, when little or no sugars are consumed for cell growth.

In one or more embodiments, a fermentation method may be characterized by inorganic-to-organic nitrogen ratio (I/O-N). Nitrogen source and inorganic-to-organic nitrogen ratio may affect cell growth and metabolism. Inorganic-to-organic nitrogen concentration ratio is based, at least in part, on the type of feedstock utilized. An inorganic nitrogen source, such as ammonium, may be combined with the feedstock or fermentation mixture to adjust the I/O-N ratio. In these or other embodiments, an organic nitrogen source, such as yeast extract, may be combined with the feedstock or fermentation mixture to adjust the I/O-N ratio. Exemplary inorganic nitrogen sources include ammonium sulfate, ammonium phosphate, ammonium hydrogen phosphate, ammonium dihydrogen phosphate, ammonium nitrate, ammonium chloride, ammonium hydroxide, ammonium acetate, ammonium bicarbonate, ammonium carbonate, ammonia, sodium nitrate, potassium nitrate, and combinations thereof. Exemplary organic nitrogen sources include peptone, yeast extract, tryptone, malt extract, protein, peptides, amino acids, urea, corn steep liquor, milk, soybean meal, soybean flour, soybean molasses, soybean milk, other seed meals, and combinations thereof.

In one or more embodiments, the I/O-N ratio of a fermentation mixture is 0 or more, in other embodiments, 0.35 or more, in other embodiments, 0.60 or more, and in other embodiments, 0.80 or more. In one or more embodiments, the I/O-N ratio of a fermentation mixture is 1.0 or less, in other embodiments, 0.80 or less, in other embodiments, 0.70 or less, and in other embodiments, 0.40 or less. In one or more embodiments, the I/O-N ratio of a fermentation mixture is in a range of from 0 or more to 1 or less, in other embodiments, from 0.2 or more to 0.8 or less, and in other embodiments, from 0.4 or more to 0.5 or less.

One or more embodiments of the invention provide a fermentation method with higher arabitol concentration using an increased I/O-N ratio. As exemplified below, higher arabitol concentrations of 36.6±1.5 g/L may be obtained at higher I/O-N ratios, and lower arabitol concentrations of 30.6±1.2 g/L may be obtained when inorganic nitrogen is not present or at a lower I/O-N ratio. This effect may be based on the different pH profiles caused by different I/O-N ratios.

In one or more embodiments, a fermentation method may be characterized by inorganic nitrogen concentration. In one or more embodiments, the inorganic nitrogen concentration of a fermentation mixture is 0 g/L or more, in other embodiments, 0.25 g/L or more, in other embodiments, 0.35 g/L or more, and in other embodiments, 0.45 g/L or more. In one or more embodiments, the inorganic nitrogen concentration of a fermentation mixture is 0.50 g/L or less, in other embodiments, 0.40 g/L or less, in other embodiments, 0.35 g/L or less, and in other embodiments, 0.25 g/L or less. In one or more embodiments, the inorganic nitrogen concentration of a fermentation mixture is in a range of from 0 g/L or more to 5 g/L or less, in other embodiments, from 0.2 g/L or more to 2 g/L or less, and in other embodiments, from 0.3 g/L or more to 1 g/L or less.

In one or more embodiments, a fermentation method may be characterized by organic nitrogen concentration. In one or more embodiments, the organic nitrogen concentration of a fermentation mixture is 0.40 g/L or more, in other embodiments, 0.45 g/L or more, in other embodiments, 0.65 g/L or more, and in other embodiments, 0.90 g/L or more. In one or more embodiments, the organic nitrogen concentration of a fermentation mixture is 1.0 g/L or less, in other embodiments, 0.65 g/L or less, in other embodiments, 0.55 g/L or less, and in other embodiments, 0.45 g/L or less. In one or more embodiments, the organic nitrogen concentration of a fermentation mixture is in a range of from 0 g/L or more to 8 g/L or less, in other embodiments, from 0.2 g/L or more to 5 g/L or less, and in other embodiments, from 0.5 g/L or more to 1 g/L or less.

In one or more embodiments, a fermentation method may be characterized by sugar composition. Exemplary sugar compositions are disclosed above with respect to the feedstock. A fermentation method may be adjusted to meet any of the above elsewhere herein disclosed sugar compositions.

In one or more embodiments, a fermentation method may be characterized by dissolved oxygen (DO) concentration. Dissolved oxygen concentration is an important factor for cell growth and product formation. Dissolved oxygen concentration may be controlled by providing a source of oxygen to a fermentation vessel. Dissolved oxygen concentration may be controlled by agitating the fermentation culture to improve oxygen transfer efficiency. Dissolved oxygen concentration may be controlled by the working volume of a fermentation vessel, where a smaller working volume is generally expected to have better oxygen transfer efficiency via surface aeration, resulting in a higher DO condition in the fermentation culture. As described herein, controlling process conditions may be automated and achieved as generally known to those skilled in the art, such as through known process control mechanisms and algorithms.

In one or more embodiments, DO may be maintained at a sufficient concentration as to ensure fast arabitol production and complete consumption of both hexoses and pentoses. Said another way, in one or more embodiments, DO may be maintained at a sufficient concentration as to not negatively affect arabitol production, cell growth, and consumption of the pentoses (xylose and arabinose). With insufficient DO concentration (e.g. <5%) the hexoses and pentoses may be converted to undesired products of ethanol and/or organic acids, instead of arabitol. The optimal DO concentration based on the above factors may be based on a particular fermentation culture. It is believed that DO significantly impacts pentose metabolism. Although the microorganisms may metabolize the hexoses under different DO conditions, the pentoses (xylose and arabinose) are generally only metabolized under more aerobic conditions.

In one or more embodiments, the dissolved oxygen concentration, which may also be referred to as air saturation, of a fermentation mixture is 3% or more, in other embodiments, 5% or more, in other embodiments, 10% or more, and in other embodiments, 15% or more. In one or more embodiments, the dissolved oxygen concentration of a fermentation mixture is 20% or less, in other embodiments, 15% or less, in other embodiments, 10% or less, and in other embodiments, 5% or less. In one or more embodiments, the dissolved oxygen concentration of a fermentation mixture is in a range of from 1% or more to 50% or less, in other embodiments, from 5% or more to 30% or less, and in other embodiments, from 10% or more to 20% or less. One or more embodiments of the invention provide a fermentation method with higher arabitol productivity using an increased dissolved oxygen concentration. Dissolved oxygen concentration may be controlled at a desired percentage or range by utilizing automatic adjustment of the agitation speed.

In one or more embodiments, a fermentation method may be characterized by pH. In one or more embodiments, the pH of a fermentation mixture is 3.0 or more, in other embodiments, 5.0 or more, in other embodiments, 6.0 or more, and in other embodiments, 7.0 or more. In one or more embodiments, the pH of a fermentation mixture is 9.0 or less, in other embodiments, 7.0 or less, in other embodiments, 6.0 or less, and in other embodiments, 4.0 or less. In one or more embodiments, the pH of a fermentation mixture is in a range of from 3.0 or more to 9.0 or less, in other embodiments, from 4.0 or more to 7.0 or less, and in other embodiments, from 5.0 or more to 6.0 or less.

In one or more embodiments, a fermentation method may be characterized by pH for a certain phase of the fermentation. In one or more embodiments, the pH of a fermentation mixture during a growth phase is in a range of from 5 or more to 9 or less, in other embodiments, from 5.5 or more to 8 or less, and in other embodiments, from 6 or more to 7 or less. In one or more embodiments, the pH of a fermentation mixture during a stationary phase is in a range of from 3 or more to 5 or less, in other embodiments, from 3.5 or more to 4.5 or less, and in other embodiments, from 3.5 or more to 4 or less.

In one or more embodiments, pH of a fermentation method may be allowed to fluctuate based on the fermentation culture progression. In one or more embodiments, pH of a fermentation method may be controlled at a desired pH by automated addition of an acid, e.g. 1N HCl, or a base, e.g. 0.5N NaOH.

As exemplified below, one or more embodiments of the invention provide a fermentation method with higher arabitol yield using lower pH. This lower pH, e.g. from 3.5 or more to 4.5 or less, may be particularly advantageous for a stationary phase.

In one or more embodiments, a fermentation method may be characterized by temperature. In one or more embodiments, the temperature of a fermentation mixture is 15° C. or more, in other embodiments, 25° C. or more, in other embodiments, 30° C. or more, and in other embodiments, 40° C. or more. In one or more embodiments, the temperature of a fermentation mixture is 50° C. or less, in other embodiments, 40° C. or less, in other embodiments, 30° C. or less, and in other embodiments, 20° C. or less. In one or more embodiments, the temperature of a fermentation mixture is in a range of from 15° C. or more to 50° C. or less, in other embodiments, from 20° C. or more to 40° C. or less, and in other embodiments, from 25° C. or more to 30° C. or less.

As disclosed above, a product stream 18 is obtained from the fermentation method. Product stream 18 includes the desired product of arabitol among other byproducts, such as ethanol, glycerol, citric acid, xylitol, mannitol, sorbitol, and acetic acid. It is desired to maximize the production of arabitol and minimize the production of byproducts. Advantageously, one or more embodiments of the invention provide a fermentation culture where all of the sugar types in a biomass may be converted to arabitol. Arabitol is a five carbon sugar alcohol with one hydroxyl group on each carbon. It is a stereoisomer of xylitol, a well-known low calorie sugar substitute. Product stream 18 may undergo one or more additional processing steps (e.g. centrifugation, purification) as generally known to those skilled in the art. A final arabitol product may be used in commercial products such as chewing gum, toothpaste, lozenges, and low calorie sweetener. Arabitol may also be a potential alternative to products utilizing xylitol, sorbitol, and erythritol.

A fermentation process and product stream thereof may be characterized by the parts of arabitol produced based on 100 total parts by weight of polyols produced by the process. In one or more embodiments, a fermentation process produces arabitol in an amount 60 parts by weight or greater, in other embodiments, 70 parts by weight or greater, in other embodiments, 80 parts by weight or greater, in other embodiments, 90 parts by weight or greater, in other embodiments, 92 parts by weight or greater, in other embodiments, 95 parts by weight or greater, and in other embodiments, 99 parts by weight or greater, based on 100 total parts by weight of polyols produced by the process.

A fermentation process and product stream thereof may be characterized by arabitol yield. In one or more embodiments, a fermentation process produces arabitol at an arabitol yield of 5% or greater, in other embodiments, 20% or greater, in other embodiments, 30% or greater, in other embodiments, 40% or greater, in other embodiments, 50% or greater, and in other embodiments, 60% or greater.

A fermentation process and product stream thereof may be characterized by percent arabitol in the product stream. In one or more embodiments, a product stream includes 60 wt. % or more arabitol, in other embodiments, 80 wt. % or more arabitol, in other embodiments, 90 wt. % or more arabitol, in other embodiments, 95 wt. % or more arabitol, and in other embodiments, 99 wt. % or more arabitol, based on the total product stream.

A fermentation process and product stream thereof may be characterized by percent arabitol with respect to non-solids in a product stream. In one or more embodiments, a product stream includes 60 wt. % or more arabitol, in other embodiments, 80 wt. % or more arabitol, in other embodiments, 90 wt. % or more arabitol, in other embodiments, 95 wt. % or more arabitol, and in other embodiments, 99 wt. % or more arabitol, based on the non-solids in the product stream.

A fermentation process and product stream thereof may be characterized by volumetric productivity of arabitol. In one or more embodiments, a fermentation process produces arabitol at a volumetric productivity of 0.2 g/L-h or greater, in other embodiments, 0.5 g/L-h or greater, in other embodiments, 0.9 g/L-h or greater, in other embodiments, 1.5 g/L-h or greater, in other embodiments, 2 g/L-h or greater, and in other embodiments, 3 g/L-h or greater. In one or more embodiments, a fermentation process produces arabitol at a volumetric productivity of 4 g/L-h or less, in other embodiments, 3 g/L-h or less, in other embodiments, 2 g/L-h or less, in other embodiments, 1.5 g/L-h or less, and in other embodiments, 1 g/L-h or less.

In one or more embodiments, a growth phase produces arabitol at a volumetric productivity of 0.2 g/L-h or greater, in other embodiments, 0.5 g/L-h or greater, in other embodiments, 0.9 g/L-h or greater, in other embodiments, 1.5 g/L-h or greater, in other embodiments, 2 g/L-h or greater, and in other embodiments, 3 g/L-h or greater. In one or more embodiments, a growth phase produces arabitol at a volumetric productivity of 4 g/L-h or less, in other embodiments, 3 g/L-h or less, in other embodiments, 2 g/L-h or less, in other embodiments, 1.5 g/L-h or less, and in other embodiments, 1 g/L-h or less.

In one or more embodiments, a stationary phase produces arabitol at a volumetric productivity of 0.2 g/L-h or greater, in other embodiments, 0.5 g/L-h or greater, in other embodiments, 0.9 g/L-h or greater, in other embodiments, 1.5 g/L-h or greater, in other embodiments, 2 g/L-h or greater, and in other embodiments, 3 g/L-h or greater. In one or more embodiments, a stationary phase produces arabitol at a volumetric productivity of 4 g/L-h or less, in other embodiments, 3 g/L-h or less, in other embodiments, 2 g/L-h or less, in other embodiments, 1.5 g/L-h or less, and in other embodiments, 1 g/L-h or less.

A fermentation process and product stream thereof may be characterized by specific productivity of arabitol. In one or more embodiments, a fermentation process produces arabitol at a specific productivity of 0.001 g/g-h or greater, in other embodiments, 0.005 g/g-h or greater, in other embodiments, 0.01 g/g-h or greater, in other embodiments, 0.03 g/g-h or greater, in other embodiments, 0.05 g/g-h or greater, and in other embodiments, 0.1 g/g-h or greater. In one or more embodiments, a fermentation process produces arabitol at a specific productivity of 0.2 g/g-h or less, in other embodiments, 0.1 g/g-h or less, in other embodiments, 0.05 g/g-h or less, in other embodiments, 0.03 g/g-h or less, and in other embodiments, 0.01 g/g-h or less.

In one or more embodiments, a growth phase produces arabitol at a specific productivity of 0.001 g/g-h or greater, in other embodiments, 0.005 g/g-h or greater, in other embodiments, 0.01 g/g-h or greater, in other embodiments, 0.03 g/g-h or greater, in other embodiments, 0.05 g/g-h or greater, and in other embodiments, 0.1 g/g-h or greater. In one or more embodiments, a growth phase produces arabitol at a specific productivity of 0.2 g/g-h or less, in other embodiments, 0.1 g/g-h or less, in other embodiments, 0.05 g/g-h or less, in other embodiments, 0.03 g/g-h or less, and in other embodiments, 0.01 g/g-h or less.

In one or more embodiments, a stationary phase produces arabitol at a specific productivity of 0.001 g/g-h or greater, in other embodiments, 0.005 g/g-h or greater, in other embodiments, 0.01 g/g-h or greater, in other embodiments, 0.03 g/g-h or greater, in other embodiments, 0.05 g/g-h or greater, and in other embodiments, 0.1 g/g-h or greater. In one or more embodiments, a stationary phase produces arabitol at a specific productivity of 0.2 g/g-h or less, in other embodiments, 0.1 g/g-h or less, in other embodiments, 0.05 g/g-h or less, in other embodiments, 0.03 g/g-h or less, and in other embodiments, 0.01 g/g-h or less.

In one or more embodiments, a fermentation process produces minimal amounts of byproducts, where minimal may be defined as less than 1 g/L. In one or more embodiments, a fermentation process produces arabitol as the sole polyol. Fewer byproducts results in easier and less costly downstream product collection and purification, to achieve a final arabitol product.

The presence and concentration of arabitol and other polyols may be measured using high performance liquid chromatography (HPLC).

In one or more embodiments, it may be desirable to remove the product stream from a fermentation process at a particular time. This may be based on a desire to maximize the arabitol in the product stream. Certain fermentation processes may begin to consume arabitol as the carbon source once the readily consumable sugars are depleted or substantially depleted. Thus, in one or more embodiments, it may be desirable to remove the product stream once the readily consumable sugars are depleted or substantially depleted.

In one or more embodiments, the product stream may be removed from a fermentation process once a certain process condition is achieved. This process condition may signal the above described transition to the fermentation process beginning to consume arabitol as the carbon source. In one or more embodiments, the product stream may be removed from a fermentation process once a process condition increases a predetermined amount.

In one or more embodiments, for a fermentation process with a measured DO concentration, the product stream may be removed from the fermentation process upon a sudden increase in the DO concentration. This may include a sudden increase above a DO concentration at which the fermentation process is being controlled. This sudden increase may then result in a drop back to the previous DO concentration. In one or more embodiments, the product stream may be removed from the fermentation process prior to the drop back to the previous DO concentration. In these embodiments, the removal of a product prior to the drop to the previous DO concentration will prevent the microorganism from consuming the arabitol product. In one or more embodiments, the product stream may be removed from the fermentation process following the drop back to the previous DO concentration.

Though the measured DO concentration may fluctuate over time based on process operations or measuring capabilities, the sudden increase will be a sharp and noticeable increase compared to prior measurements of the DO. Quantitative measurements of the increase for one or more embodiments are provided below.

In one or more embodiments, the product stream may be removed from a fermentation process once a process condition, e.g. DO concentration, increases by a relative amount of 100% (e.g. from 5% DO to 10% DO) or approximate thereto, in other embodiments, 200% or approximate thereto, in other embodiments, 300% or approximate thereto, in other embodiments, 400% or approximate thereto, in other embodiments, 500% or approximate thereto, in other embodiments, 600% or approximate thereto, and in other embodiments, 800% or approximate thereto. In one or more embodiments, the product stream may be removed from a fermentation process once a process condition, e.g. DO concentration, increases by a relative amount of 100% or more, in other embodiments, 200% or more, in other embodiments, 300% or more, in other embodiments, 400% or more, in other embodiments, 500% or more, in other embodiments, 600% or more, and in other embodiments, 800% or more.

In one or more embodiments, the product stream may be removed from a fermentation process once a process condition, e.g. DO concentration, increases by an absolute amount of 5% (e.g. from 5% DO to 10% DO) or approximate thereto, in other embodiments, 10% or approximate thereto, in other embodiments, 15% or approximate thereto, in other embodiments, 20% or approximate thereto, in other embodiments, 25% or approximate thereto, in other embodiments, 30% or approximate thereto, and in other embodiments, 40% or approximate thereto. In one or more embodiments, the product stream may be removed from a fermentation process once a process condition, e.g. DO concentration, increases by an absolute amount of 5% or more, in other embodiments, 10% or more, in other embodiments, 15% or more, in other embodiments, 20% or more, in other embodiments, 25% or more, in other embodiments, 30% or more, and in other embodiments, 40% or more.

For any of the above increasing amounts, in one or more embodiments, the timeframe for measuring the increase may be over a span of 1 minute, in other embodiments, 3 minutes, in other embodiments, 5 minutes, in other embodiments, 10 minutes, in other embodiments, 30 minutes, in other embodiments, 60 minutes, in other embodiments, 90 minutes, and in other embodiments, 120 minutes.

In one or more embodiments, a product stream may be removed from a fermentation process once a process condition increases above a predetermined amount. In one or more embodiments, a product stream may be removed from a fermentation process the DO concentration increases above an absolute amount of 10%, in other embodiments, above an absolute amount of 15%, in other embodiments, above an absolute amount of 20%, in other embodiments, above an absolute amount of 25%, in other embodiments, above an absolute amount of 30%, and in other embodiments, above an absolute amount of 35%.

In one or more embodiments, the product stream may be removed from a fermentation process once a process condition decreases a predetermined amount.

In one or more embodiments, once a certain process condition is achieved, a modification may be made to feedstock 12. In one or more embodiments, this may include increasing the amount of carbon source in feedstock 12 as to not allow the fermentation to begin to consume arabitol as the carbon source. In one or more embodiments, this may include adding a next batch of feedstock 12 as to not allow the fermentation to begin to consume arabitol as the carbon source.

In one or more embodiments, the product stream may be removed from a fermentation process once a particular arabitol concentration is achieved. This arabitol concentration may be based on a calculation based on protein concentration in feedstock, and particular sugars concentrations in the feedstock and/or in the fermentation culture. In one or more embodiments, the product stream may be removed from a fermentation process when the arabitol concentration reaches 40 g/L, or approximate thereto, in other embodiments, 60 g/L, or approximate thereto, and in other embodiments, 100 g/L, or approximate thereto.

In light of the foregoing, it should be appreciated that the present invention advances the art by providing improved production of arabitol. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Chemicals

Peptone, yeast extract, malt extract, $K_2SO_4$, $CuSO_4$, $Na_2S_2O_3 \cdot 5H_2O$ and $MgSO_4 \cdot 7H_2O$ were purchased from Sigma-Aldrich; agar, glucose, fructose, $H_3BO_3$, HPLC grade water and $(NH_4)_2SO_4$ from Fisher Scientific; $K_2HPO_4$ from Merck; arabinose from Acros organics; and $KH_2PO_4$ from EMD Chemicals.

Preparation of Soybean Flour and Soybean Hull Hydrolysates

Soybean flour hydrolysate (SFH) was prepared by hydrolyzing soybean flour using the enzyme produced by *Aspergillus niger*. The produced enzyme contained different enzyme activities including cellulase, xylanase, pectinase, α-galactosidase, and sucrase. Soybean flour was first dry sterilized at 160° C. for 2 h. The enzyme solution was adjusted to pH 4.8 and then added to soy flour at a 4:1 ratio (v/w). Enzyme hydrolysis was carried out at 50° C. and pH 4.8 for 24 h. Hydrolysate was then separated from the protein-enriched solids by centrifugation at 7500×g for 10 min. A similar procedure was used for soybean hull hydrolysis (SHH) except that the soybean hull was sterilized by autoclaving at 121° C. for 15 min instead of the dry heat sterilization of soybean flour.

Microorganism and Inoculum Preparation

*D. hansenii* SBP-1 (NRRL Y-7483) was obtained from USDA ARS culture collection (Peoria, Ill.). Culture was maintained on agar plates containing 10 g/L glucose, 3 g/L yeast extract, 3 g/L malt extract, 5 g/L peptone and 20 g/L agar. The same medium without the agar was used for inoculum preparation for the shake flask studies. A loop of cells was transferred from an agar plate to 50 ml medium in a 250 ml Erlenmeyer flask covered with cheese cloth-sandwiched cotton. The culture was grown at 30° C. for 24 h in a shaker operating at 250 rpm. The inoculum thus prepared was added at 5% of the final culture volume in the subsequent studies.

Studies in Shake Flasks

All shake flask studies were made at 30±0.5° C. and 250 rpm rotation speed, with 50 ml initial broths in 250 ml Erlenmeyer flasks. The only exception was the study of culture volume effect, where different broth volumes were used in 500 ml flasks. Water loss by evaporation during the culture experiments was monitored with simulating systems containing only water. Measured concentrations of cell, sugars and arabitol were adjusted accordingly. Two batches of SFH were used in the studies. One contained 41.9±2.7 g/L total sugars (15.6±1.1 g/L glucose, 12.3±0.7 g/L fructose, 11.4±0.9 g/L galactose, 2.1±0.5 g/L xylose, and 0.5±0.2 g/L arabinose) and 1.8±0.1 g/L organic nitrogen with a calculated C/N ratio of 9.3; the other contained 38.7±1.6 g/L total sugars (13.7±1.3 g/L glucose, 11.5±0.9 g/L fructose, 10.7±0.8 g/L galactose, 2.2±0.6 g/L xylose, and 0.6±0.3 g/L arabinose) and 1.9±0.1 g/L organic nitrogen with a C/N ratio of 8.1. The latter was used in the culture volume effect experiments. The former was used in all other studies for medium effects.

Medium Composition

Some experiments were made with SFH alone as the medium. One set of experiments were made to study the effect of mineral supplementation by adding $MgSO_4 \cdot 7H_2O$ (1 g/L), $K_2HPO_4$ (2.4 g/L) and $CaCl_2 \cdot 2H_2O$ (0.5 g/L) to SFH, individually in three systems and all together in the fourth system. Further experiments were made by supplementing SFH with sugars and/or an inorganic nitrogen source $(NH4)_2SO_4$ to study separate medium effects on arabitol production.

Arabitol Production

The results from the shake flask studies were used for a set of examples. Fermentations were conducted in 2.5-L New Brunswick Bioflo 110 fermentors with 1-L working volume. The medium used was SFH supplemented with SHH and $K_2HPO_4$ (2.4 g/L). Total sugar concentration and organic nitrogen concentration were 80 and 2.8 g/L, respectively, with a C/N ratio of 28.5. One system was made with no pH control; the other was made with controlled slow decrease of pH to 4.0 in 36 h and then maintained at 4.0, by automatic acid (1N HCl) or base (0.5N NaOH) addition. Temperature was maintained at 30° C. throughout the fermentation using a heating jacket. Both fermentors were aerated with 1 L/min of 0.2-μm filter-sterilized air. DO was allowed to drop naturally along cell growth to 5% air saturation and then controlled at 5% by automatic adjustment of the agitation speed, which was initially set at 400 rpm.

Analytical Methods

Cell Dry-Weight Concentration Measurement

Samples were taken at regular intervals from the culture systems studied. The samples were then centrifuged at 10000×g for 10 min (model 5415D, Eppendorf, Hauppauge, NY). The supernatants were collected and frozen for future analyses of sugars and arabitol. The cell pellets were washed twice with deionized water and then measured for cell dry weights after drying cells at 100° C. overnight in a hot air oven (Binder-world, Bohemia, NY).

Sugar and Arabitol Concentrations

Sugars and arabitol were measured using a high performance liquid chromatography (HPLC) system (Shimadzu LC 10A) with a refractive index detector (RID-10A). A carbohydrate column (Supelcogel Pb, 30 cm×7.8 mm) with a guard column (No. 59345, 50 mm×4.6 mm) was used at 80° C. The mobile phase was HPLC grade water at a flowrate of 0.5 mL/min. Typical retention times for glucose, xylose, galactose, arabinose, fructose and arabitol were 17.3, 18.3, 19.5, 20.7, 22.1 and 32.1 min, respectively. Calibration curves for converting the peak areas to concentrations were established with standard solutions of pure sugars and arabitol.

Organic Nitrogen Concentration

The Kjeldahl method was used to measure the nitrogen contents of samples. A liquid hydrolysate sample diluted to 50 ml, containing 10 to 200 mg/L protein, was added to a flask and digested with 10 ml reagent containing 134 ml/L concentrated $H_2SO_4$, 134 g/L $K_2SO_4$ and 7.3 g/L $CuSO_4$. The digestion was carried out to completion, until the reaction mixture became a clear solution. The digested sample was allowed to cool and then added with 30 ml water and 10 ml of a distillation reagent containing 500 g/L NaOH and 25 g/L $Na_2S_2O_3.5H_2O$. This mixture was distilled using a distillation unit (RapidStill 1, Labconco, Kansas City, Mo.) to produce ammonia gas, which was absorbed in 0.1 N $H_3BO_3$. Then the $H_3BO_3$ solution was titrated using 0.1 N $H_2SO_4$ to find the nitrogen concentration in the sample.

Example 1—SFH as Medium

Figure 3A:
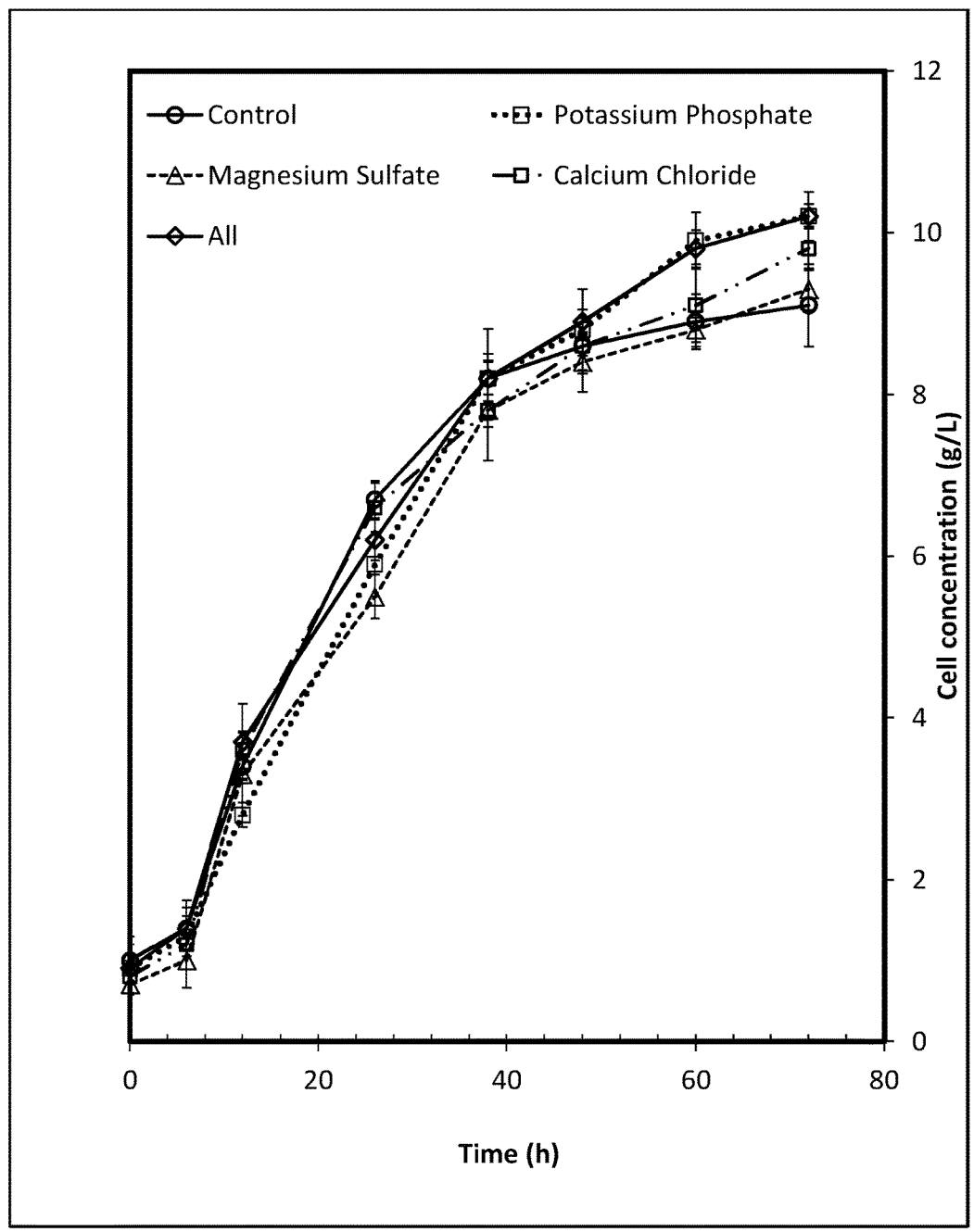
FIG. 3A is a graph showing cell concentration for examples of one or more embodiments of the invention.
Figure 3B:
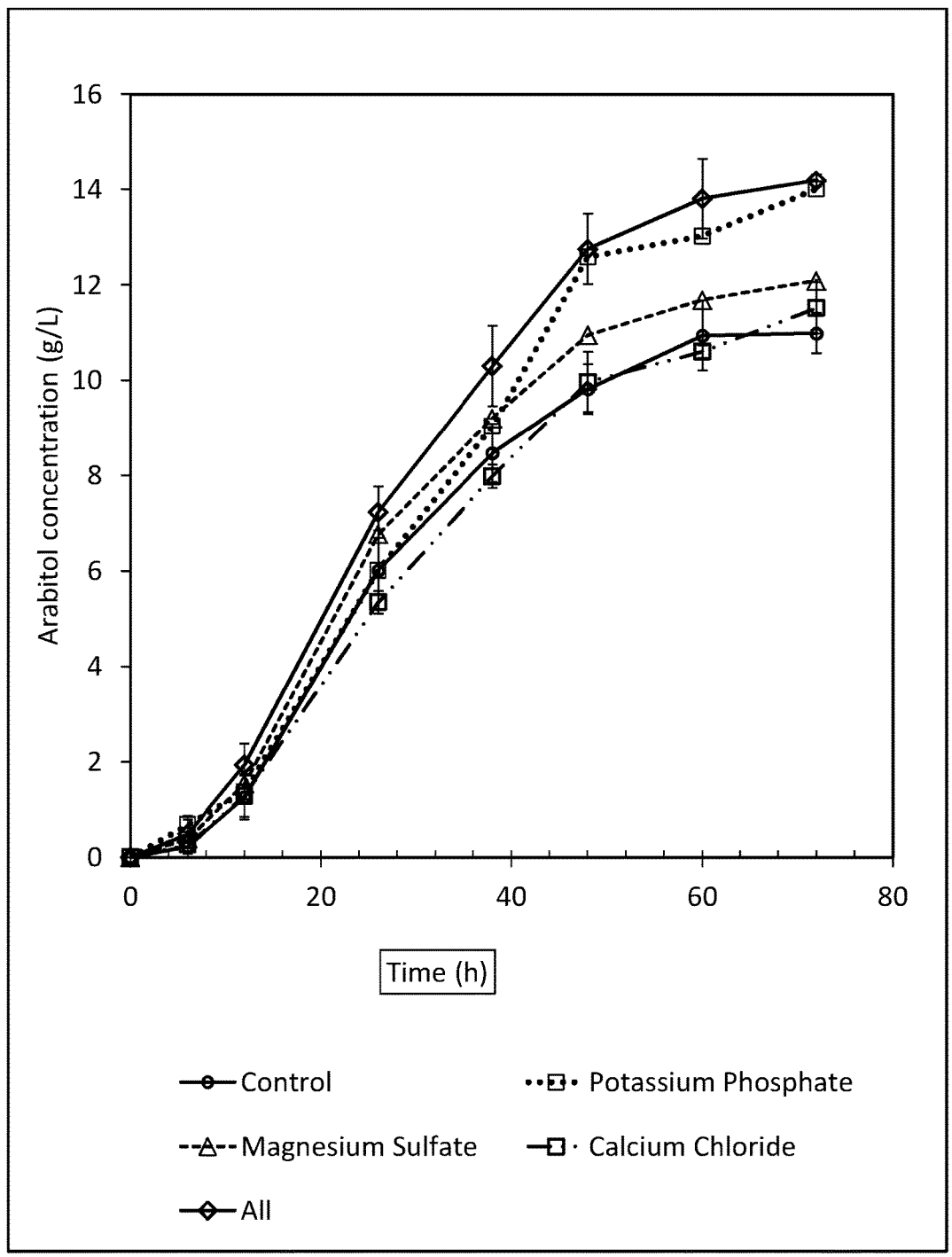
FIG. 3B is a graph showing arabitol concentration for examples of one or more embodiments of the invention.

The initial total sugar concentration was 41.9±2.7 g/L. After 3 days, 10.8±0.8 g/L arabitol was produced, cell concentration reached 11.2±0.6 g/L, and 3.5±0.4 g/L sugars remained. Consumption profiles of individual sugars was determined; SFH consisted of 5 main sugars: glucose, fructose and galactose were 3 major hexoses and xylose and arabinose were 2 minor pentoses. Catabolite repression was seen; the yeast consumed the hexoses with a clear order of preference: glucose>fructose>galactose. Hexoses were completely depleted. Consumption of the two pentoses was not evident in this system; their concentrations remained essentially constant Example 2—Mineral Supplementation Though SFH alone was found to support cell growth and arabitol production by *D. hansenii*, it was also determined if supplementation of certain minerals would improve rates and/or yields. Results obtained with or without addition of $MgSO_4.7H_2O$ (1 g/L), $K_2HPO_4$ (2.4 g/L) and $CaCl_{2.2}H_2O$ (0.5 g/L), individually or together, to SFH are shown in FIG. 3A and FIG. 3B. Calcium chloride and magnesium sulfate supplementations were found not to significantly affect the final cell ($p=0.34$) and arabitol concentrations ($p=0.19$) achieved. However, addition of potassium phosphate improved the final arabitol and cell concentrations. Maximum cell concentration in presence of potassium phosphate was 10.2±0.4 g/L, compared to 9.2±0.3 g/L in the negative control of no mineral supplements ($p<0.02$). The effect seemed to be even stronger on arabitol production than on cell growth. Final arabitol concentration was increased from 11±0.6 g/L to 14.1±0.4 g/L with the addition of potassium phosphate ($p<0.001$). When all three mineral nutrients were supplemented in SFH, the results were similar to the system with only potassium phosphate addition, which supports that the positive effect was due to potassium phosphate addition.

Example 3—C/N Ratio 5 media were prepared as shown in Table 1.

TABLE 1

| | Varied compositions of media used in shake flask study for effect of C/N ratio. | | | |
|---|---|---|---|---|
| Medium | Total sugar (g/L) | Total carbon (g/L) | SFH organic N (g/L) | C/N ratio |
| 1 | 26.8 | 10.72 | 0.45 | 23.8 |
| 2 | 49.9 | 19.96 | 0.60 | 33.3 |
| 3 | 76.7 | 30.86 | 0.60 | 51.4 |
| 4 | 94.5 | 37.80 | 0.60 | 63.0 |
| 5 | 76.8 | 30.72 | 0.90 | 34.1 |

Figure 4A:
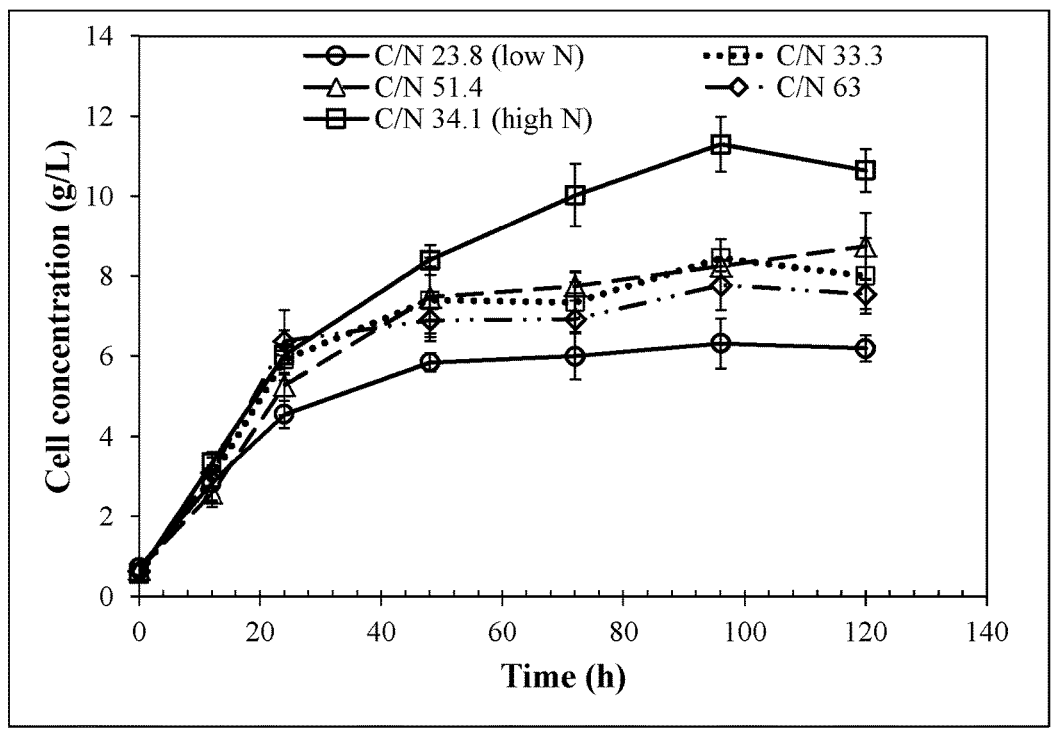
FIG. 4A is a graph showing cell concentration for examples of one or more embodiments of the invention.
Figure 4B:
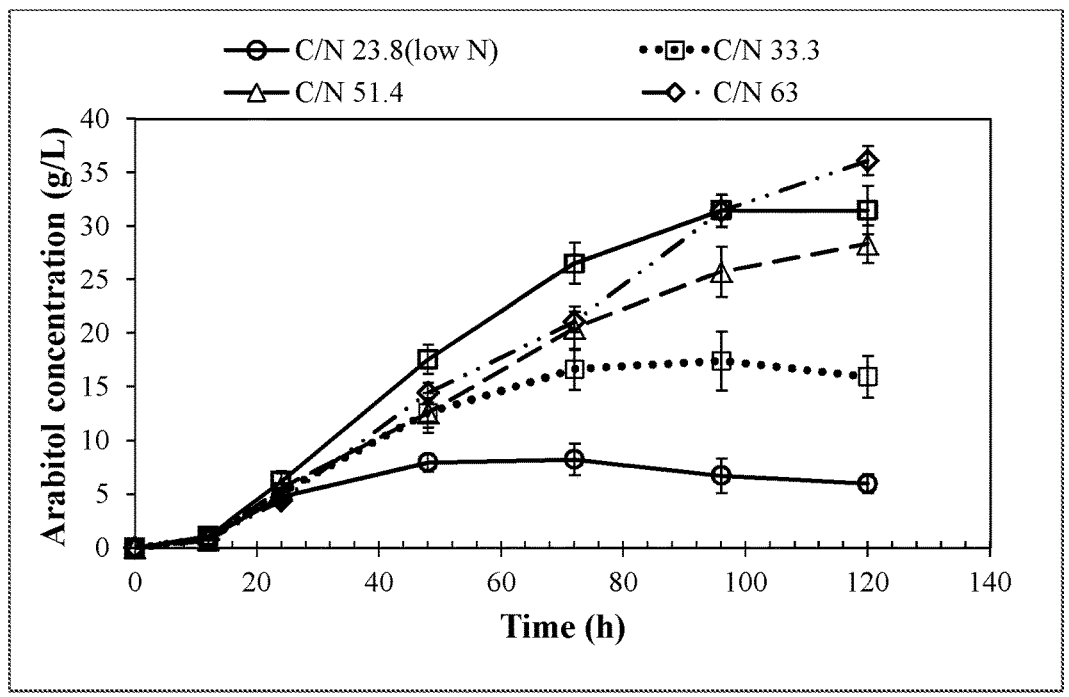
FIG. 4B is a graph showing arabitol concentration for examples of one or more embodiments of the invention.

The C/N ratio was varied from 23.8 to 63.0. The nitrogen source was only from SFH while the carbon source was from SFH and additional sugars. Cell and arabitol concentration profiles obtained in these systems are shown in FIGS. 4A and 4B, respectively. The initial total sugar concentrations, concentrations of consumed sugars at the end of the run-times (120 h), and the corresponding yields of arabitol from the consumed sugars are further compared in FIG. 4C to show the effects of different C/N ratios. Maximum cell concentrations were found to correlate with the nitrogen source concentrations. Highest cell concentration of 11.3 g/L was achieved with the highest N concentration of 0.9 g/L in the high N system (C/N 34.1) and the lowest cell concentration of about 6 g/L was achieved with the lowest N concentration of 0.45 g/L present in the low N system (C/N 23.8). The other three systems, with C/N ratios of 33.3, 51.4 and 63.0, all had 0.60 g/L N and similar maximum cell concentrations of 7.8 to 8.8 g/L.

Effects of C/N ratio on arabitol production were also seen. In the system of lowest C/N ratio of 23.8, arabitol concentration plateaued at 48 h, after active cell growth stopped. At this low C/N ratio, the medium was C-limiting (although xylose and arabinose would remain unconsumed). In the two systems with the next levels of C/N ratios, 33.3 and 34.1, the additional sugars supported arabitol production for about 1 or 2 more days. In the two systems of still higher C/N ratios, 51.4 and 63, arabitol production continued throughout the 5-day fermentation in both growth and stationary phases. The highest arabitol production of 36 g/L was achieved in the system with the highest C/N ratio of 63.

Figure 4C:
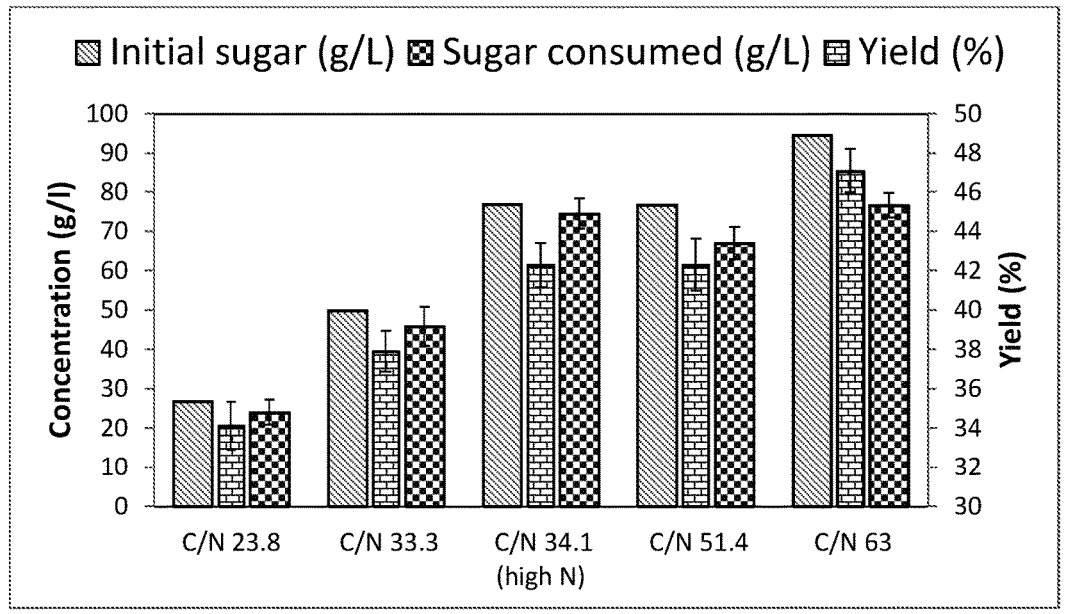
FIG. 4C is a graph showing comparison of the initial and consumed concentrations of total sugars and arabitol yield from the consumed sugars after 120 h for examples of one or more embodiments of the invention.

As shown in FIG. 4C, arabitol yield also increased with increasing C/N ratio: lowest at 34% with C/N ratio of 23.8 and highest at 47% with C/N ratio of 63. This correlation may indicate the arabitol yield was higher when produced during the stationary phase, when no sugars were consumed for cell growth. In the system with a C/N ratio of 63, 94 g/L total sugar was provided but only 77 g/L was consumed. So, the yield may be even higher if arabitol production was allowed to proceed longer (at stationary phase) till complete exhaustion of consumable sugars.

Example 4—Inorganic to Organic Nitrogen Ratio 5 media were prepared as shown in Table 2.

TABLE 2

Varied compositions of media used in shake flask study for effect of inorganic-to-organic nitrogen concentration ratio.

| Medium | Total sugar (g/L) | Total N (g/L) | SFH organic N (g/L) | Inorganic $NH_4^+$—N (g/L) | Inorganic/ organic N ratio (g/L) |
|---|---|---|---|---|---|
| 1 | 76.8 | 0.90 | 0.45 | 0.45 | 1.00 |
| 2 | 76.8 | 0.90 | 0.50 | 0.40 | 0.80 |
| 3 | 76.8 | 0.90 | 0.55 | 0.35 | 0.64 |
| 4 | 76.8 | 0.90 | 0.65 | 0.25 | 0.39 |
| 5 | 76.8 | 0.90 | 0.90 | 0.00 | 0.00 |

Figure 5A:
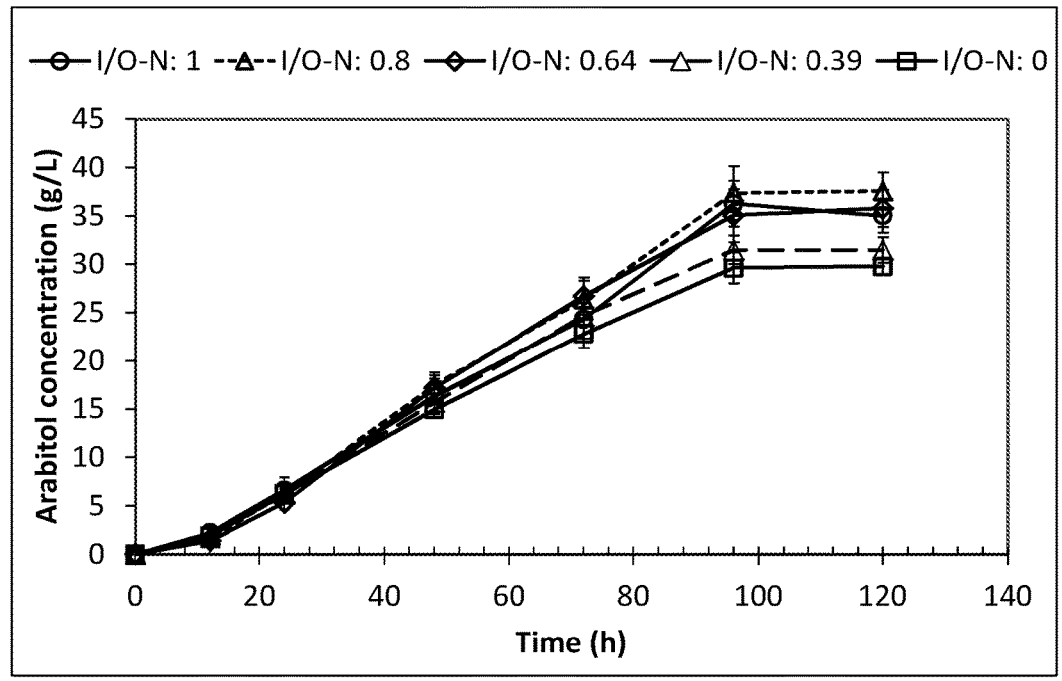
FIG. 5A is a graph showing arabitol concentration for examples of one or more embodiments of the invention.

As seen in Table 2, the media used had the same total sugars (76.8 g/L) and total N (0.9 g/L) but varying inorganic-to-organic nitrogen ratios, I/O-N, from 0 to 1. The C/N ratio was 34.1. This medium was N-limiting. Accordingly, cell concentration profiles were very similar for all similar systems described herein except that maximum cell concentrations reached at lower I/O-N ratios were slightly higher For I/O-N ratios of 0, 0.39 and 0.64, cells grew to 10.6±0.52 g/L; for I/O-N ratios of 0.8 and 1.0, maximum cell concentrations were 9.3±0.65 g/L (p<0.043). As shown in FIG. 5A, arabitol production during the growth phase, up to 72 h, was also similar for all the systems but it differed during the stationary phase. Higher arabitol concentrations of 36.6±1.5 g/L were obtained at higher I/O-N ratios of 0.64, 0.8 and 1.0; and lower arabitol concentrations of 30.6±1.2 g/L were found when inorganic nitrogen was not present or at a low I/O-N ratio (0.39). These results suggest that including some inorganic nitrogen source was helpful for arabitol production at this C/N ratio. This effect could be associated with the different pH profiles caused by different I/O-N ratios.

Figure 5B:
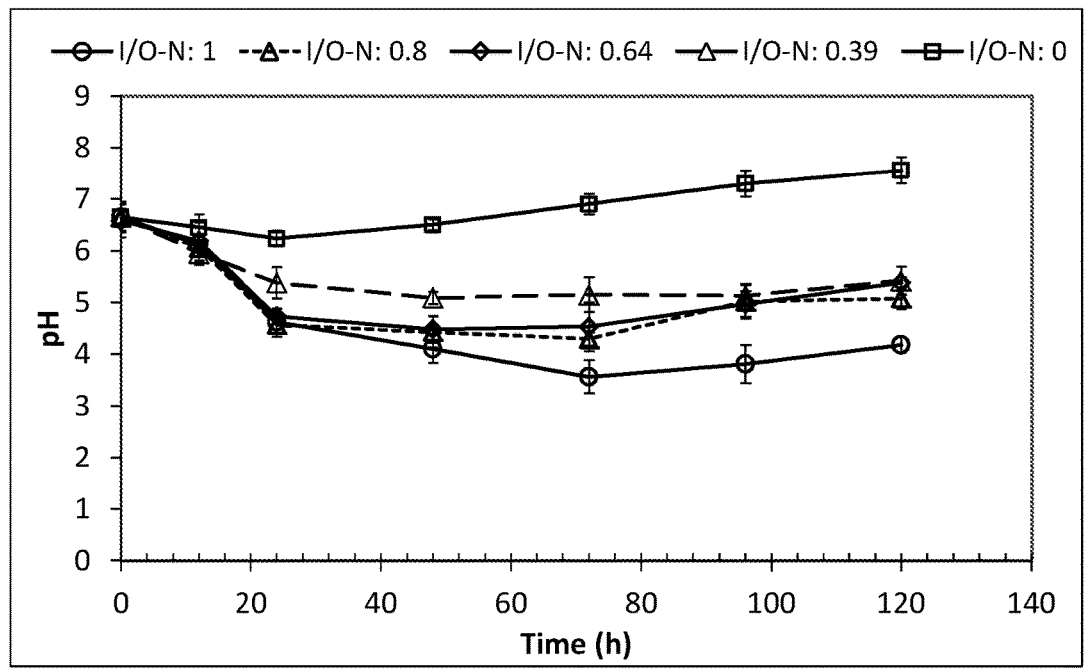
FIG. 5B is a graph showing pH change for examples of one or more embodiments of the invention.
Figure 5C:
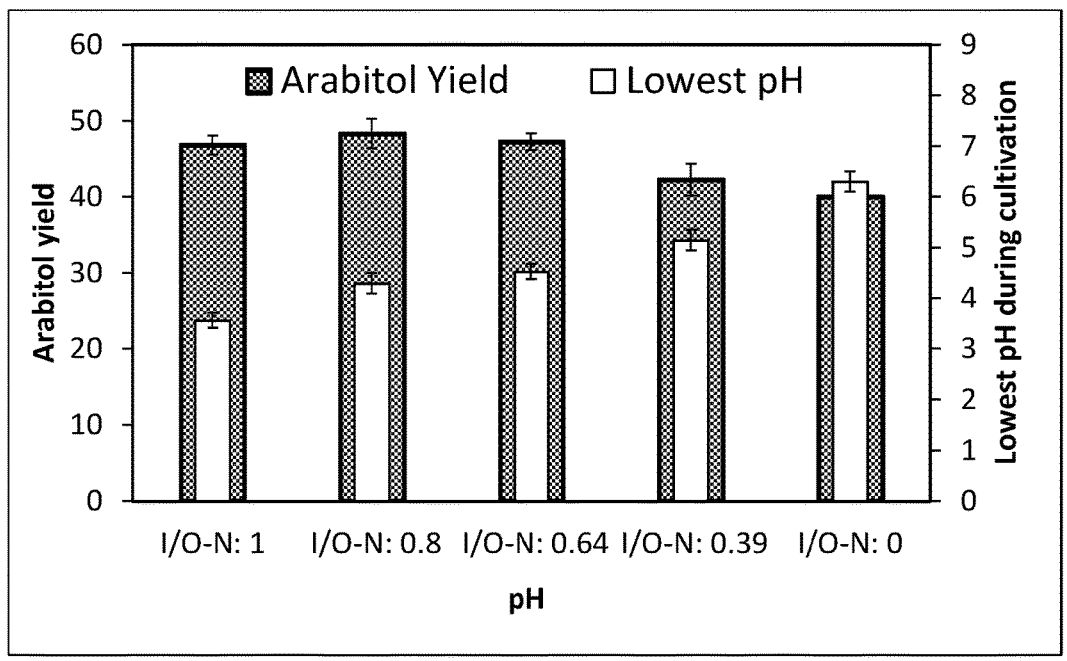
FIG. 5C is a graph showing final arabitol yields and lowest pH values for examples of one or more embodiments of the invention.

The pH profiles are shown in FIG. 5B and the arabitol yields achieved and the lowest pH recorded for the 5 systems are compared in FIG. 5C. pH depended strongly on the I/O-N ratio. When the inorganic nitrogen (from ammonium) was higher in the system, the recorded lowest pH was lower because ammonia consumption led to pH decrease. The lowest pH was 3.6±0.1 in the system with the highest amount of inorganic N source (I/O-N ratio=1.0). In the system with only organic N source (I/O-N ratio=0), the lowest pH was 6.3±0.2 and, except for the first 24 h, pH increased with time. As shown in FIG. 5C, arabitol yield correlated with the lowest pH in the systems. Arabitol yields were similar, averaged around 47.5%, in systems with lowest pH in the range of 3.5-4.5 (I/O-N ratios of 0.64-1.00). Arabitol yields were significantly lower in systems with lowest pH averaging 5.15 and 6.30, respectively.

Example 5—Sugar Composition 6 media were prepared as shown in Table 3.

TABLE 3

Varied compositions of media used in shake flask study for effect of sugar composition.

| | Glucose | | Pentose |
|---|---|---|---|
| Medium | % Total sugars | % Hexoses | (% total sugars) |
| 1 | 18.5 | 25 | 25 |
| 2 | 25.8 | 31 | 20 |
| 3 | 33.1 | 38 | 12 |
| 4 | 40.5 | 50 | 20 |
| 5 | 55.2 | 58 | 5 |
| 6 | 67.0 | 75 | 10 |

Figure 6A:
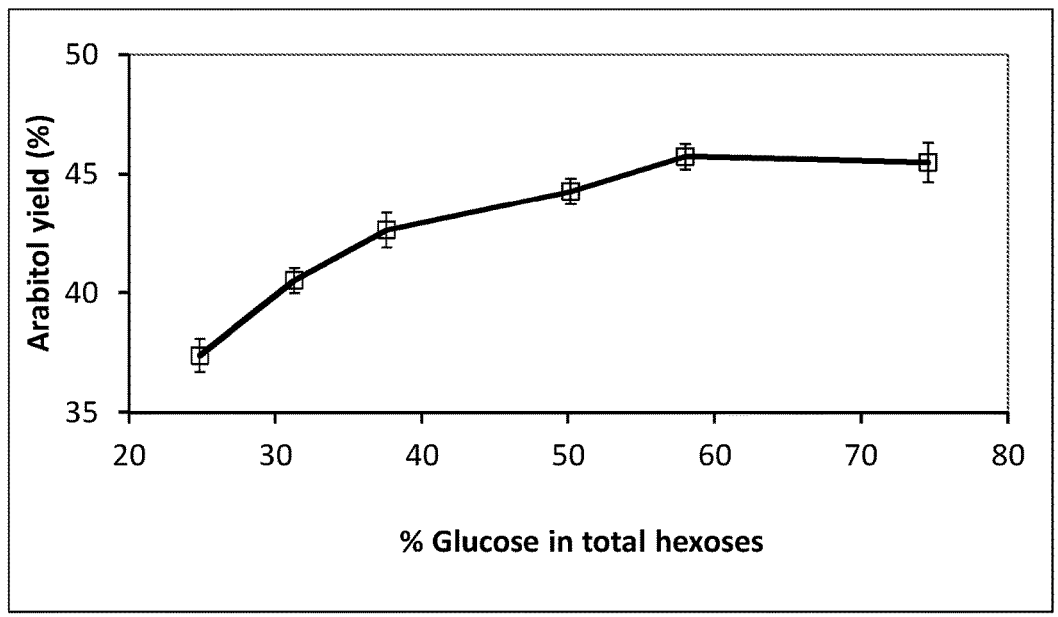
FIG. 6A is a graph showing final arabitol yields for examples of one or more embodiments of the invention.
Figure 6B:
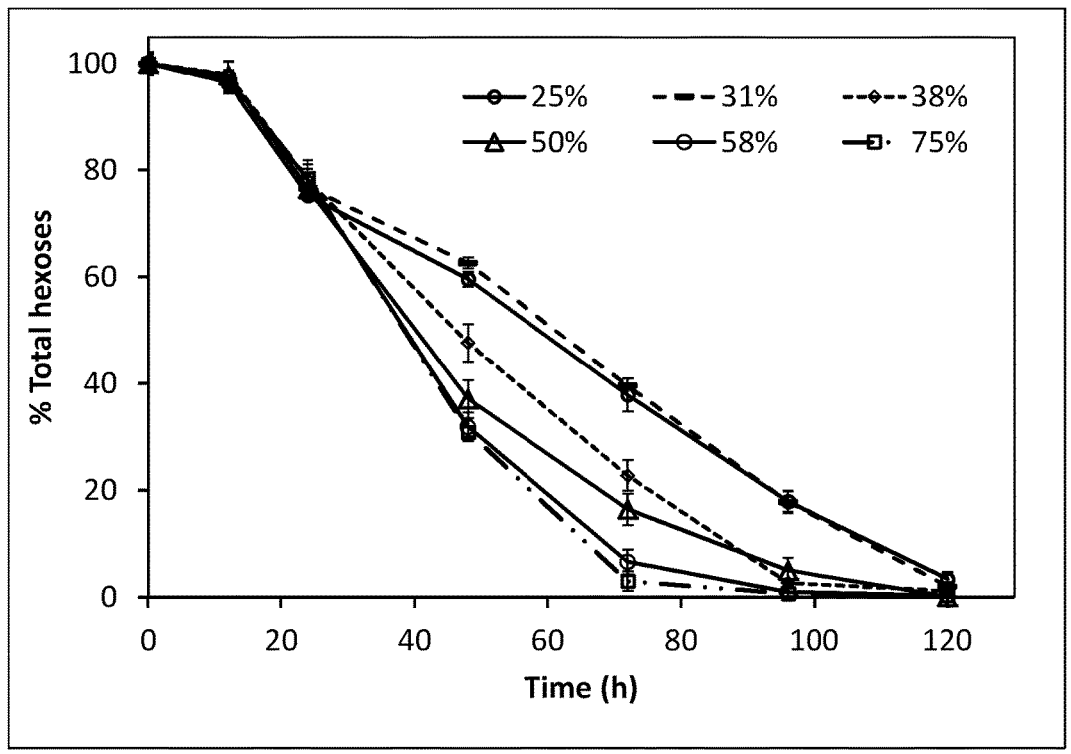
FIG. 6B is a graph showing time profiles of total hexose consumption for examples of one or more embodiments of the invention.

In these systems, xylose and arabinose concentrations did not show clear changes to indicate consumption in the 5-day fermentation. On the other hand, all 3 hexoses were completely consumed according to the order of preference described herein, i.e., glucose, then fructose, and finally galactose. Arabitol yields obtained in systems with different glucose %, with glucose % given as % of the total hexoses, in the range of 25% to 75%, are shown in FIG. 6A. Total hexose consumption with time is compared in FIG. 6B. Both sugar consumption rate and arabitol yield depended on the glucose %, and were higher at increasing glucose %. Arabitol yield of 45.3±0.9% was achieved in the systems where glucose made up at least 50% of the hexoses.

Example 6—Dissolved Oxygen

Figure 7:
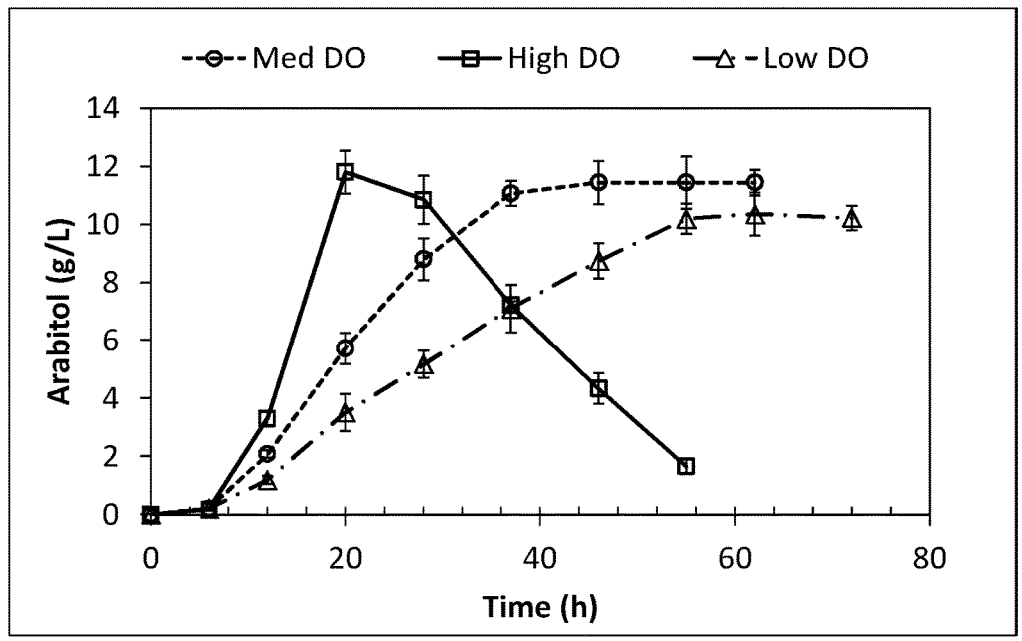
FIG. 7 is a graph showing arabitol concentration for examples of one or more embodiments of the invention.

Different medium volumes (40, 75 and 100 ml) used in 500 ml flasks were expected to cause different levels of dissolved oxygen concentrations (DO) in the fermentation medium due to different ratios of liquid surface area to volume. Cell growth, total sugar consumption, and arabitol production were monitored. Lower culture volumes, i.e., higher DO, were clearly better for faster cell growth and higher cell concentrations. Maximum cell concentration was 20 g/L in the system of the lowest culture volume (40 ml). It decreased with increasing volume and was only about 9 g/L in the system with 100 ml initial volume. In the lowest volume (highest DO) system, sugars were almost depleted in only 20-28 h and arabitol production was maximal at 20 h with an arabitol concentration of 11.8 g/L. The corresponding arabitol yield was 35% and volumetric productivity was 0.59 g/L-h. In systems of the medium and largest volumes, maximum arabitol concentrations reached 11.4 and 10.7 g/L at 46 and 72 h, respectively, significantly later than the time required in the lowest volume system. Higher DO condition was clearly beneficial for achieving high arabitol productivity. In at least the highest DO medium, once the readily consumable sugars were depleted, cells were seen to consume arabitol as carbon source (FIG. 7). In the lowest volume system, this arabitol consumption could support further cell growth, under no limitation of nitrogen or other essential growth nutrients. Therefore, timing for product harvesting may be designed accordingly for actual production processes.

DO concentration also appeared to affect the yeast's pentose consumption. Concentration profiles of xylose and arabinose in systems of different culture volumes were determined. These two pentoses were not noticeably consumed in the system of largest culture volume (100 ml in 500 ml flasks). However, pentose consumption occurred in the two systems of lower volumes (higher DO conditions) after exhaustion of hexoses. Between the two pentoses, xylose was preferred over arabinose. Arabitol production may be conducted at high enough DO to ensure fast production and complete consumption of both hexoses and pentoses.

Example 7—Controlled pH

Figure 8A:
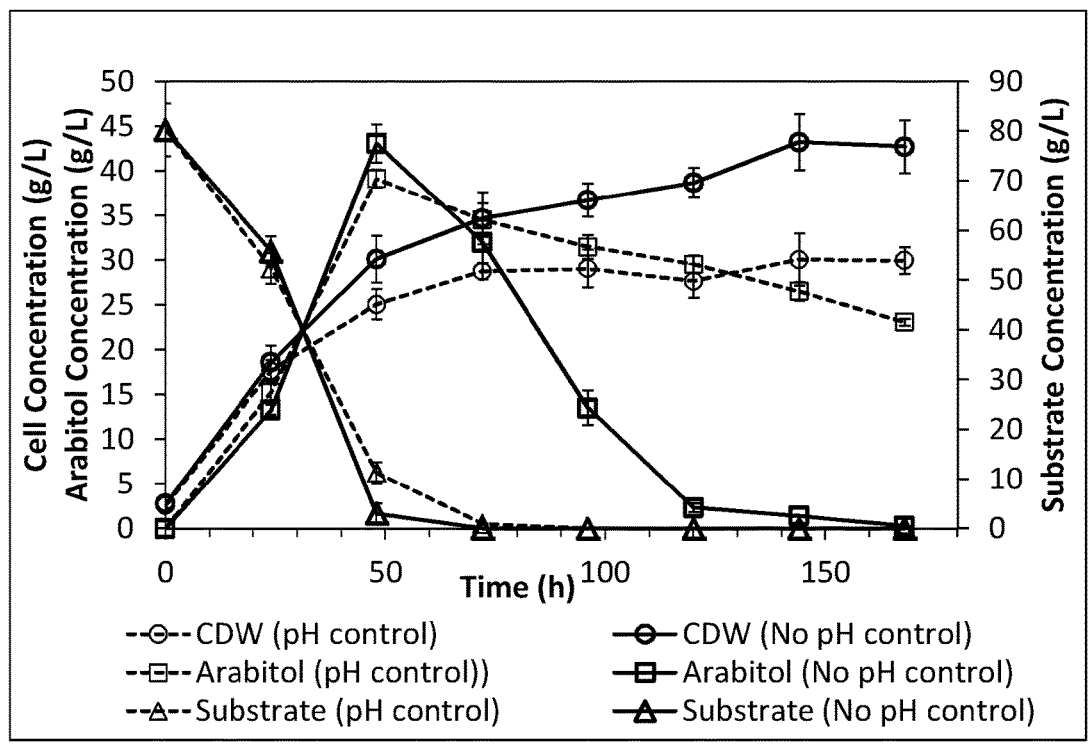
FIG. 8A is a graph showing arabitol concentration, cell concentration, and substrate concentration for examples of one or more embodiments of the invention.
Figure 8B:
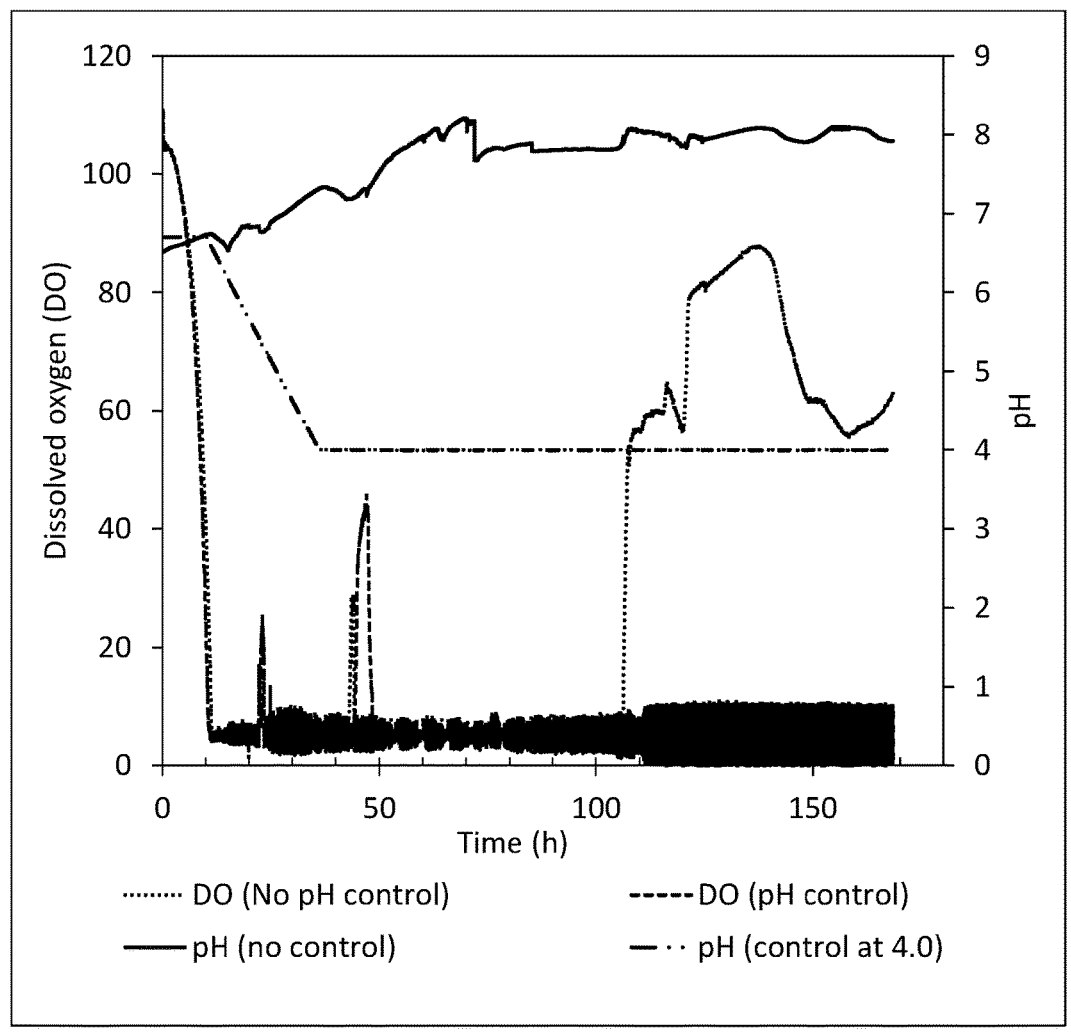
FIG. 8B is a graph showing pH and dissolved oxygen for examples of one or more embodiments of the invention.

A first fermentation system had an initial pH of about 6.6, which was maintained for about 10 hours. The pH was then gradually lowered to 4 over about 24 hours by acid addition. A second fermentation system had an initial pH of about 6.5 and the pH thereafter was not controlled. Profiles of cell dry-weight concentration (CDW), total sugar, and arabitol concentrations for each system are shown in FIG. 8A. pH and DO profiles are shown in FIG. 8B. In both systems, DO dropped to the 5% control point in about 10 h and the yeast consumed almost all sugars and produced maximal arabitol concentrations in about 48 h. Until 24 h, cell growth and arabitol production were similar in the two systems but differed afterwards. For the fermentation without pH control, pH increased during the first 3 days to as high as 8.1 due to consumption of organic nitrogen. In the controlled pH system, the lower pH negatively affected cell growth and arabitol production. At 48 h, cell and arabitol concentrations in this low pH system were 25 and 39 g/L, respectively, lower than the corresponding concentrations of 30 and 43 g/L in the system without pH control. While utilizing a stationary phase at lower pH, for example at 3.5-4.5, may give higher arabitol yield for the stationary phase (see FIG. 5C), this low pH may not be beneficial for arabitol production during the growth phase. For this Example, The fermentation without pH control was easy to operate and provided superior arabitol production.

With a C/N ratio of 28.5, these mediums were still C-limiting so that after the sugars were depleted at about 48 h, the yeast started to consume arabitol as carbon source. This rate of consumption was particularly high in the system of no pH control (and it supported further cell growth using the remaining nitrogen source). Having a real-time process signal that indicates this switch to arabitol consumption may guide the harvesting time and avoid product loss. From the DO profiles in FIG. 8B, this switch of cell metabolism was detected in both fermentations at around 45-48 h when DO suddenly increased before dropping back to the 5% control point. If harvested at 48 h in the system of no pH control, the arabitol yield was 54% and the volumetric and specific productivities were 0.90 g/L-h and 0.033 g/g-h, respectively.

Various modifications and alterations that do not depart from the scope and spirit of this invention will become apparent to those skilled in the art. This invention is not to be duly limited to the illustrative embodiments set forth herein.

What is claimed is:

1. A method for producing arabitol comprising:
providing a fermentation culture having a yeast and a carbon source, wherein the fermentation culture has dissolved oxygen, wherein the yeast is one or more naturally-occurring osmophilic yeast selected from the species *Debaryomyces hansenii, Metschnikowia zobellii, Geotrichum candidum, Geotrichum fermentans*, and *Geotrichum* cucujoidarum;
allowing the yeast to ferment the carbon source, which thereby produces a product comprising arabitol;
controlling the dissolved oxygen concentration of the fermentation culture at a predetermined amount following the step of allowing the yeast to ferment the carbon source;
monitoring the dissolved oxygen concentration during the step of allowing the yeast to ferment the carbon source, wherein the step of monitoring continues until the dissolved oxygen concentration indicates that the fermentation culture is beginning to consume the arabitol, wherein the dissolved oxygen concentration indicating that the fermentation culture is beginning to consume the arabitol includes the dissolved oxygen concentration increasing a relative amount of 100% or more above the predetermined amount in the step of controlling; and
collecting the product comprising arabitol from the fermentation culture after the step of monitoring indicates that the fermentation culture is beginning to consume the arabitol.

2. The method of claim 1, wherein the dissolved oxygen concentration indicating that the fermentation culture is beginning to consume the arabitol includes the dissolved oxygen concentration increasing to an absolute amount of 15% or more.

3. The method of claim 1, further comprising:
modifying the fermentation culture after the step of monitoring indicates that the fermentation culture is beginning to consume the arabitol.

4. The method of claim 3, wherein the step of modifying the fermentation culture includes adding an additional carbon source to the fermentation culture.

5. A method for producing arabitol comprising:
providing a fermentation culture having a yeast and a carbon source, wherein the yeast is one or more naturally-occurring osmophilic yeast selected from the species *Debaryomyces hansenii, Metschnikowia zobellii, Geotrichum candidum, Geotrichum fermentans*, and *Geotrichum* cucujoidarum;
allowing the yeast to ferment the carbon source;
monitoring a process condition during the step of allowing the yeast to ferment the carbon source;
modifying the fermentation culture after a predetermined change in the process condition being monitored in the step of monitoring has occurred; and
collecting a product comprising arabitol from the fermentation culture after a predetermined change in the process condition being monitored in the step of monitoring has occurred, wherein the yeast and the carbon source are provided by a first batch of a feedstock containing the yeast and the carbon source, wherein the step of modifying the fermentation culture includes adding to the fermentation culture a second batch of the feedstock containing additional amounts of the yeast and the carbon source.

6. The method of claim 5, wherein the process condition is the arabitol concentration of the fermentation culture, wherein the predetermined change in the process condition is a higher arabitol concentration.

7. A method for producing arabitol comprising:
allowing an enzyme to hydrolyze a biomass comprising one or more of soybean flour, soybean hull, soybean molasses, and soybean okara, to obtain a hydrolysate;
providing the hydrolysate as a carbon source for a fermentation culture having a yeast therein, wherein the yeast is one or more naturally-occurring osmophilic yeast selected from the species *Debaryomyces han-*

*senii, Metschnikowia zobellii, Geotrichum candidum, Geotrichum fermentans,* and *Geotrichum* cucujoidarum;

allowing the yeast to ferment the hydrolysate;

adding a potassium-containing mineral following the step of allowing the yeast to ferment the hydrolysate and prior to a subsequent step of collecting a product, wherein the arabitol concentration of the collected product is higher compared to the corresponding method wherein the potassium-containing mineral is not added; and collecting a product having arabitol, following the step of adding the potassium-containing mineral.

8. A method for producing arabitol comprising:

allowing an enzyme to hydrolyze a biomass comprising one or more of soybean flour, soybean hull, soybean molasses, and soybean okara, to obtain a hydrolysate;

providing the hydrolysate as a carbon source for a fermentation culture having a yeast therein, wherein the yeast is one or more naturally-occurring osmophilic yeast selected from the species *Debaryomyces hansenii, Metschnikowia zobellii, Geotrichum candidum, Geotrichum fermentans,* and *Geotrichum* cucujoidarum;

allowing the yeast to ferment the hydrolysate;

adding a potassium-containing mineral following the step of allowing the yeast to ferment the hydrolysate and prior to a subsequent step of collecting a product, wherein the arabitol concentration of the collected product is higher compared to the corresponding method wherein a calcium-containing mineral or a magnesium-containing mineral is added; and collecting a product having arabitol, following the step of adding the potassium-containing mineral.

9. A method for producing arabitol comprising:

allowing an enzyme to hydrolyze a biomass comprising one or more of soybean flour, soybean hull, soybean molasses, and soybean okara, to obtain a hydrolysate;

providing the hydrolysate as a carbon source for a fermentation culture having a yeast therein, wherein the yeast is one or more naturally-occurring osmophilic yeast selected from the species *Debaryomyces hansenii, Metschnikowia zobellii, Geotrichum candidum, Geotrichum fermentans,* and *Geotrichum* cucujoidarum;

allowing the yeast to ferment the hydrolysate; and collecting a product having arabitol, following the step of allowing the yeast to ferment the hydrolysate;

wherein the dissolved oxygen concentration during the step of allowing the yeast to ferment the hydrolysate is sufficiently high as to achieve substantially complete fermentation of all hexoses and pentoses in the hydrolysate.

10. The method of claim 7, wherein the hydrolysate includes one or more of at least 1 wt. % amino acids, at least 1 wt. % peptides, and at least 1 wt. % proteins, thereby minimizing the need for cellular amino acid synthesis in the yeast, thereby increasing arabitol production by maintaining the available intermediates from the pentose phosphate pathway for the production of arabitol.

11. A method for producing arabitol comprising:

combining a feedstock having a carbon source with a yeast to form a fermentation culture to ferment the carbon source with the yeast by a fermentation process, the fermentation process having a growth phase and a stationary phase, wherein the yeast is one or more naturally-occurring osmophilic yeast selected from the species *Debaryomyces hansenii, Metschnikowia zobellii, Geotrichum candidum, Geotrichum fermentans,* and *Geotrichum* cucujoidarum;

maintaining the growth phase at a pH in a range of from 5.5 or more to 8 or less;

maintaining the stationary phase at a pH in a range of from 3.5 or more to 4.5 or less; and obtaining a product including arabitol, wherein the arabitol yield of the method is greater than the arabitol yield of the corresponding method that does not include steps of maintaining the growth phase at a pH in a range of from 5.5 or more to 8 or less and maintaining the stationary phase at a pH in a range of from 3.5 or more to 4.5 or less.

12. The method of claim 11, further comprising the step of adding an additional carbon source to the fermentation culture thereby preventing the consumption of arabitol as a carbon source, wherein the method achieves increasing arabitol production in both the growth phase and the stationary phase.

* * * * *